US012773247B2

(12) United States Patent
Schneider et al.

(10) Patent No.: US 12,773,247 B2
(45) **Date of Patent: *Oct. 27, 2026**

(54) MATRIX IMPLANT

(71) Applicant: SI-Bone Inc., Santa Clara, CA (US)

(72) Inventors: Bret W. Schneider, San Jose, CA (US); Roxanne Simon, San Jose, CA (US); Derek P. Lindsey, San Jose, CA (US); Scott A Yerby, Montara, CA (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/927,238

(22) Filed: Oct. 25, 2024

(65) Prior Publication Data

US 2025/0040972 A1 Feb. 6, 2025

Related U.S. Application Data

(63) Continuation of application No. 17/443,388, filed on Jul. 26, 2021, now Pat. No. 12,161,374, which is a (Continued)

(51) Int. Cl.
*A61F 2/44* (2006.01)
*A61B 17/70* (2006.01)
(Continued)

(52) U.S. Cl.
CPC .......... *A61B 17/84* (2013.01); *A61B 17/7055* (2013.01); *A61F 2/44* (2013.01); *A61F 2002/2839* (2013.01); *A61F 2002/30115* (2013.01); *A61F 2002/30149* (2013.01); *A61F 2002/30154* (2013.01); *A61F 2002/30156* (2013.01); *A61F 2002/30171* (2013.01); *A61F 2002/30604* (2013.01); *A61F 2002/30995* (2013.01); *A61F 2002/4495* (2013.01)

(58) Field of Classification Search
CPC ...... A61B 17/7055; A61F 2/44; A61F 2/4405; A61F 2/4455
See application file for complete search history.

(56) References Cited

U.S. PATENT DOCUMENTS 1,951,278 A 3/1934 Ericsson
2,136,471 A 11/1938 Schneider
(Continued)

FOREIGN PATENT DOCUMENTS

CN 1128944 A 8/1996
CN 1190882 A 8/1998
(Continued)

OTHER PUBLICATIONS

Acumed; Acutrak Headless Compression Screw (product information); 12 pgs; ©2005; retrieved Sep. 25, 2014 from http://www.rcsed.ac.uk/fellows/lvanrensburg/classification/surgtech/acumed/manuals/acutrak-brochure%200311.pdf.
(Continued)

*Primary Examiner* — Ellen C Hammond
(74) *Attorney, Agent, or Firm* — Shay Glenn LLP

(57) ABSTRACT

Implants for the fusion or fixation of two bone segments are described. For example, the implants can be used for the fusion or fixation of the sacroiliac joint. The implants can have a matrix structure, have a rectilinear cross-sectional area, and have a curvature.

18 Claims, 10 Drawing Sheets

Related U.S. Application Data continuation of application No. 16/263,971, filed on Jan. 31, 2019, now Pat. No. 11,071,573, which is a continuation of application No. 15/593,208, filed on May 11, 2017, now Pat. No. 10,194,962, which is a continuation of application No. 14/859,005, filed on Sep. 18, 2015, now Pat. No. 9,662,157.

(60) Provisional application No. 62/052,379, filed on Sep. 18, 2014.

(51) Int. Cl.
*A61B 17/84* (2006.01)
*A61F 2/28* (2006.01)
*A61F 2/30* (2006.01)

(56) References Cited

U.S. PATENT DOCUMENTS

| | | | |
|---|---|---|---|
| 2,243,717 | A | 5/1941 | Moreira |
| 2,414,882 | A | 1/1947 | Longfellow |
| 2,562,419 | A | 7/1951 | Ferris |
| 2,675,801 | A | 4/1954 | Bambara et al. |
| 2,697,433 | A | 12/1954 | Zehnder |
| 3,076,453 | A | 2/1963 | Tronzo |
| 3,506,982 | A | 4/1970 | Steffee |
| 3,694,821 | A | 10/1972 | Moritz |
| 3,709,218 | A | 1/1973 | Halloran |
| 3,744,488 | A | 7/1973 | Cox |
| 4,059,115 | A | 11/1977 | Jumashev et al. |
| 4,156,943 | A | 6/1979 | Collier |
| 4,197,645 | A | 4/1980 | Scheicher |
| 4,292,964 | A | 10/1981 | Ulrich |
| 4,341,206 | A | 7/1982 | Perrett et al. |
| 4,344,190 | A | 8/1982 | Lee et al. |
| 4,399,813 | A | 8/1983 | Barber |
| 4,423,721 | A | 1/1984 | Otte et al. |
| 4,475,545 | A | 10/1984 | Ender |
| 4,501,269 | A | 2/1985 | Bagby |
| 4,569,338 | A | 2/1986 | Edwards |
| 4,612,918 | A | 9/1986 | Slocum |
| 4,622,959 | A | 11/1986 | Marcus |
| 4,630,601 | A | 12/1986 | Harder et al. |
| 4,638,799 | A | 1/1987 | Moore |
| 4,657,550 | A | 4/1987 | Daher |
| 4,743,256 | A | 5/1988 | Brantigan |
| 4,773,402 | A | 9/1988 | Asher et al. |
| 4,787,378 | A | 11/1988 | Sodhi |
| 4,790,303 | A | 12/1988 | Steffee |
| 4,834,757 | A | 5/1989 | Brantigan |
| 4,846,162 | A | 7/1989 | Moehring |
| 4,877,019 | A | 10/1989 | Vives |
| 4,878,915 | A | 11/1989 | Brantigan |
| 4,898,186 | A | 2/1990 | Ikada et al. |
| 4,904,261 | A | 2/1990 | Dove et al. |
| 4,950,270 | A | 8/1990 | Bowman et al. |
| 4,961,740 | A | 10/1990 | Ray et al. |
| 4,969,888 | A | 11/1990 | Scholten et al. |
| 4,981,481 | A | 1/1991 | Kranz et al. |
| 5,034,011 | A | 7/1991 | Howland |
| 5,034,013 | A | 7/1991 | Kyle et al. |
| 5,035,697 | A | 7/1991 | Frigg |
| 5,041,118 | A | 8/1991 | Wasilewski |
| 5,053,035 | A | 10/1991 | McLaren |
| 5,059,193 | A | 10/1991 | Kuslich |
| 5,066,296 | A | 11/1991 | Chapman et al. |
| 5,098,434 | A | 3/1992 | Serbousek |
| 5,102,414 | A | 4/1992 | Kirsch |
| 5,108,397 | A | 4/1992 | White |
| 5,122,141 | A | 6/1992 | Simpson et al. |
| 5,139,498 | A | 8/1992 | Astudillo Ley |
| 5,139,500 | A | 8/1992 | Schwartz |
| 5,147,367 | A | 9/1992 | Ellis |
| 5,147,402 | A | 9/1992 | Bohler et al. |
| 5,190,551 | A | 3/1993 | Chin et al. |
| 5,197,961 | A | 3/1993 | Castle |
| 5,242,444 | A | 9/1993 | MacMillan |
| 5,298,254 | A | 3/1994 | Prewett et al. |
| 5,334,205 | A | 8/1994 | Cain |
| 5,380,325 | A | 1/1995 | Lahille et al. |
| 5,390,683 | A | 2/1995 | Pisharodi |
| 5,433,718 | A | 7/1995 | Brinker |
| 5,443,466 | A | 8/1995 | Shah |
| 5,458,638 | A | 10/1995 | Kuslich et al. |
| 5,470,334 | A | 11/1995 | Ross et al. |
| 5,480,402 | A | 1/1996 | Kim |
| 5,569,249 | A | 10/1996 | James et al. |
| 5,591,235 | A | 1/1997 | Kuslich |
| 5,593,409 | A | 1/1997 | Michelson |
| 5,607,424 | A | 3/1997 | Tropiano |
| 5,609,635 | A | 3/1997 | Michelson |
| 5,609,636 | A | 3/1997 | Kohrs et al. |
| 5,626,616 | A | 5/1997 | Speece |
| 5,643,264 | A | 7/1997 | Sherman et al. |
| 5,645,599 | A | 7/1997 | Samani |
| 5,658,337 | A | 8/1997 | Kohrs et al. |
| 5,667,510 | A | 9/1997 | Combs |
| 5,669,909 | A | 9/1997 | Zdeblick et al. |
| 5,672,178 | A | 9/1997 | Petersen |
| 5,683,391 | A | 11/1997 | Boyd |
| 5,709,683 | A | 1/1998 | Bagby |
| 5,713,904 | A | 2/1998 | Errico et al. |
| 5,716,358 | A | 2/1998 | Ochoa et al. |
| 5,725,581 | A | 3/1998 | Brånemark |
| 5,743,912 | A | 4/1998 | LaHille et al. |
| 5,759,035 | A | 6/1998 | Ricci |
| 5,766,174 | A | 6/1998 | Perry |
| 5,766,252 | A | 6/1998 | Henry et al. |
| 5,766,261 | A | 6/1998 | Neal et al. |
| 5,788,699 | A | 8/1998 | Bobst et al. |
| 5,800,440 | A | 9/1998 | Stead |
| 5,868,749 | A | 2/1999 | Reed |
| 5,897,556 | A | 4/1999 | Drewry et al. |
| 5,899,906 | A | 5/1999 | Schenk |
| 5,928,239 | A | 7/1999 | Mirza |
| 5,941,885 | A | 8/1999 | Jackson |
| 5,961,522 | A | 10/1999 | Mehdizadeh |
| 5,961,554 | A | 10/1999 | Janson et al. |
| 6,010,507 | A | 1/2000 | Rudloff |
| 6,015,409 | A | 1/2000 | Jackson |
| 6,030,162 | A | 2/2000 | Huebner et al. |
| 6,053,916 | A | 4/2000 | Moore |
| 6,056,749 | A | 5/2000 | Kuslich |
| 6,066,175 | A | 5/2000 | Henderson et al. |
| 6,086,589 | A | 7/2000 | Kuslich et al. |
| 6,096,080 | A | 8/2000 | Nicholson et al. |
| 6,120,292 | A | 9/2000 | Buser et al. |
| 6,120,504 | A | 9/2000 | Brumback et al. |
| 6,129,730 | A | 10/2000 | Bono et al. |
| 6,143,031 | A | 11/2000 | Knothe et al. |
| 6,197,062 | B1 | 3/2001 | Fenlin |
| 6,206,924 | B1 | 3/2001 | Timm |
| 6,210,442 | B1 | 4/2001 | Wing et al. |
| 6,214,049 | B1 | 4/2001 | Gayer et al. |
| 6,221,074 | B1 | 4/2001 | Cole et al. |
| 6,224,607 | B1 | 5/2001 | Michelson |
| 6,241,732 | B1 | 6/2001 | Overaker et al. |
| 6,264,657 | B1 | 7/2001 | Urbahns et al. |
| 6,270,528 | B1 | 8/2001 | McKay |
| 6,287,343 | B1 | 9/2001 | Kuslich et al. |
| 6,302,885 | B1 | 10/2001 | Essiger |
| 6,302,914 | B1 | 10/2001 | Michelson |
| 6,306,140 | B1 | 10/2001 | Siddiqui |
| 6,319,253 | B1 | 11/2001 | Ackeret et al. |
| 6,406,498 | B1 | 6/2002 | Tormala et al. |
| 6,409,768 | B1 | 6/2002 | Tepic et al. |
| 6,436,139 | B1 | 8/2002 | Shapiro et al. |
| 6,451,020 | B1 | 9/2002 | Zucherman et al. |
| 6,471,707 | B1 | 10/2002 | Miller et al. |
| 6,485,518 | B1 | 11/2002 | Cornwall et al. |
| 6,497,707 | B1 | 12/2002 | Bowman et al. |
| 6,517,541 | B1 | 2/2003 | Sesic |
| 6,520,969 | B2 | 2/2003 | Lambrecht et al. |
| 6,524,314 | B1 | 2/2003 | Dean et al. |

(56) References Cited

U.S. PATENT DOCUMENTS

| | | | |
|---|---|---|---|
| 6,527,775 | B1 | 3/2003 | Warburton |
| 6,551,343 | B1 | 4/2003 | Törmälli et al. |
| 6,556,857 | B1 | 4/2003 | Estes et al. |
| 6,558,386 | B1 | 5/2003 | Cragg |
| 6,565,566 | B1 | 5/2003 | Wagner et al. |
| 6,575,899 | B1 | 6/2003 | Foley et al. |
| 6,575,991 | B1 | 6/2003 | Chesbrough et al. |
| 6,579,293 | B1 | 6/2003 | Chandran |
| 6,582,431 | B1 | 6/2003 | Ray |
| 6,582,467 | B1 | 6/2003 | Teitelbaum et al. |
| 6,595,998 | B2 | 7/2003 | Johnson et al. |
| 6,602,293 | B1 | 8/2003 | Biermann et al. |
| 6,605,090 | B1 | 8/2003 | Trieu et al. |
| 6,607,530 | B1 | 8/2003 | Carl et al. |
| 6,620,163 | B1 | 9/2003 | Michelson |
| 6,635,059 | B2 | 10/2003 | Randall et al. |
| 6,666,868 | B2 | 12/2003 | Fallin |
| 6,669,529 | B1 | 12/2003 | Scaries |
| 6,673,075 | B2 | 1/2004 | Santilli |
| 6,692,501 | B2 | 2/2004 | Michelson |
| 6,712,852 | B1 | 3/2004 | Chung et al. |
| 6,723,099 | B1 | 4/2004 | Goshert |
| 6,723,100 | B2 | 4/2004 | Biedermann et al. |
| 6,740,118 | B2 | 5/2004 | Eisermann et al. |
| 6,743,257 | B2 | 6/2004 | Castro |
| D493,533 | S | 7/2004 | Blain |
| 6,793,656 | B1 | 9/2004 | Mathews |
| 6,827,740 | B1 | 12/2004 | Michelson |
| 6,984,235 | B2 | 1/2006 | Huebner |
| 6,989,033 | B1 | 1/2006 | Schmidt |
| 6,991,461 | B2 | 1/2006 | Gittleman |
| 6,993,406 | B1 | 1/2006 | Cesarano et al. |
| 7,018,416 | B2 | 3/2006 | Hanson et al. |
| 7,118,579 | B2 | 10/2006 | Michelson |
| 7,147,666 | B1 | 12/2006 | Grisoni |
| 7,175,663 | B1 | 2/2007 | Stone |
| 7,211,085 | B2 | 5/2007 | Michelson |
| 7,223,269 | B2 | 5/2007 | Chappuis |
| 7,300,439 | B2 | 11/2007 | May |
| 7,314,488 | B2 | 1/2008 | Reiley |
| 7,335,205 | B2 | 2/2008 | Aeschlimann et al. |
| 7,338,500 | B2 | 3/2008 | Chappuis |
| 7,396,365 | B2 | 7/2008 | Michelson |
| 7,452,359 | B1 | 11/2008 | Michelson |
| 7,452,369 | B2 | 11/2008 | Barry |
| 7,481,831 | B2 | 1/2009 | Bonutti |
| 7,527,649 | B1 | 5/2009 | Blain |
| 7,534,254 | B1 | 5/2009 | Michelson |
| 7,537,616 | B1 | 5/2009 | Branch et al. |
| 7,569,054 | B2 | 8/2009 | Michelson |
| 7,569,059 | B2 | 8/2009 | Cerundolo |
| 7,601,155 | B2 | 10/2009 | Petersen |
| 7,608,097 | B2 | 10/2009 | Kyle |
| 7,608,098 | B1 | 10/2009 | Stone et al. |
| 7,648,509 | B2 | 1/2010 | Stark |
| 7,686,805 | B2 | 3/2010 | Michelson |
| 7,699,852 | B2 | 4/2010 | Frankel et al. |
| 7,708,761 | B2 | 5/2010 | Petersen |
| 7,727,235 | B2 | 6/2010 | Contiliano et al. |
| 7,758,646 | B2 | 7/2010 | Khandkar et al. |
| 7,780,704 | B2 | 8/2010 | Markworth et al. |
| 7,846,162 | B2 | 12/2010 | Nelson et al. |
| 7,850,732 | B2 | 12/2010 | Heinz |
| 7,857,832 | B2 | 12/2010 | Culbert et al. |
| 7,887,565 | B2 | 2/2011 | Michelson |
| 7,892,265 | B2 | 2/2011 | Perez-Cruet et al. |
| 7,901,439 | B2 | 3/2011 | Horton |
| 7,909,832 | B2 | 3/2011 | Michelson |
| 7,922,765 | B2 | 4/2011 | Reiley |
| 7,942,879 | B2 | 5/2011 | Christie et al. |
| 7,951,176 | B2 | 5/2011 | Grady et al. |
| 8,052,728 | B2 | 11/2011 | Hestad |
| 8,062,365 | B2 | 11/2011 | Schwab |
| 8,066,705 | B2 | 11/2011 | Michelson |
| 8,066,709 | B2 | 11/2011 | Michelson |
| 8,092,505 | B2 | 1/2012 | Sommers |
| 8,142,481 | B2 | 3/2012 | Warnick |
| 8,202,305 | B2 | 6/2012 | Reiley |
| 8,221,499 | B2 | 7/2012 | Lazzara et al. |
| 8,257,398 | B2 | 9/2012 | Jackson |
| 8,268,099 | B2 | 9/2012 | O'Neill et al. |
| 8,308,779 | B2 | 11/2012 | Reiley |
| 8,308,783 | B2 | 11/2012 | Morris et al. |
| 8,317,862 | B2 | 11/2012 | Troger et al. |
| 8,348,950 | B2 | 1/2013 | Assell et al. |
| 8,350,186 | B2 | 1/2013 | Jones et al. |
| 8,353,932 | B2 | 1/2013 | Jackson |
| 8,388,667 | B2 | 3/2013 | Reiley et al. |
| 8,394,129 | B2 | 3/2013 | Morgenstern Lopez |
| 8,398,635 | B2 | 3/2013 | Vaidya |
| 8,398,682 | B2 | 3/2013 | Jackson et al. |
| 8,414,648 | B2 | 4/2013 | Reiley |
| 8,425,570 | B2 | 4/2013 | Reiley |
| 8,430,930 | B2 | 4/2013 | Hunt |
| 8,444,693 | B2 | 5/2013 | Reiley |
| 8,449,585 | B2 | 5/2013 | Wallenstein et al. |
| 8,467,851 | B2 | 6/2013 | Mire et al. |
| 8,470,004 | B2 | 6/2013 | Reiley |
| 8,475,505 | B2 | 7/2013 | Nebosky et al. |
| 8,529,608 | B2 | 9/2013 | Terrill et al. |
| 8,597,299 | B2 | 12/2013 | Farr et al. |
| 8,608,802 | B2 | 12/2013 | Bagga et al. |
| D697,209 | S | 1/2014 | Walthall et al. |
| 8,641,737 | B2 | 2/2014 | Matthis et al. |
| 8,641,766 | B2 | 2/2014 | Donner et al. |
| 8,663,298 | B2 | 3/2014 | Keyer et al. |
| 8,663,332 | B1 | 3/2014 | To et al. |
| 8,672,986 | B2 | 3/2014 | Klaue et al. |
| 8,734,462 | B2 | 5/2014 | Reiley et al. |
| 8,778,026 | B2 | 7/2014 | Mauldin |
| 8,840,623 | B2 | 9/2014 | Reiley |
| 8,840,651 | B2 | 9/2014 | Reiley |
| 8,845,693 | B2 | 9/2014 | Smith et al. |
| 8,858,601 | B2 | 10/2014 | Reiley |
| 8,888,827 | B2 | 11/2014 | Harper et al. |
| 8,894,685 | B2 | 11/2014 | Mickiewicz et al. |
| 8,926,670 | B2 | 1/2015 | Jackson |
| 8,936,623 | B2 | 1/2015 | Jackson |
| 8,945,190 | B2 | 2/2015 | Culbert et al. |
| 8,945,193 | B2 | 2/2015 | Kirschman |
| 8,951,254 | B2 | 2/2015 | Mayer et al. |
| 8,951,293 | B2 | 2/2015 | Glazer et al. |
| 8,951,295 | B2 | 2/2015 | Matityahu et al. |
| 8,961,571 | B2 | 2/2015 | Lee et al. |
| 8,979,911 | B2 | 3/2015 | Martineau et al. |
| 8,986,348 | B2 | 3/2015 | Reiley |
| RE45,484 | E | 4/2015 | Foley et al. |
| 9,039,743 | B2 | 5/2015 | Reiley |
| 9,044,321 | B2 | 6/2015 | Mauldin et al. |
| 9,060,876 | B1 | 6/2015 | To et al. |
| 9,089,371 | B1 | 7/2015 | Faulhaber |
| D738,498 | S | 9/2015 | Frey et al. |
| 9,131,955 | B2 | 9/2015 | Swofford |
| 9,149,286 | B1 | 10/2015 | Greenhalgh et al. |
| 9,173,692 | B1 | 11/2015 | Kaloostian |
| 9,198,676 | B2 | 12/2015 | Pilgeram et al. |
| 9,220,535 | B2 | 12/2015 | Röbling et al. |
| 9,314,286 | B2 | 4/2016 | Bottlang et al. |
| 9,314,348 | B2 | 4/2016 | Emstad |
| 9,358,047 | B2 | 6/2016 | Mishra et al. |
| 9,358,057 | B1 | 6/2016 | Whipple et al. |
| 9,375,243 | B1 | 6/2016 | Vestgaarden |
| 9,375,323 | B2 | 6/2016 | Reiley |
| 9,445,852 | B2 | 9/2016 | Sweeney |
| 9,451,999 | B2 | 9/2016 | Simpson et al. |
| 9,452,065 | B1 | 9/2016 | Lawson |
| 9,486,264 | B2 | 11/2016 | Reiley et al. |
| 9,492,201 | B2 | 11/2016 | Reiley |
| 9,498,264 | B2 | 11/2016 | Harshman et al. |
| 9,510,872 | B2 | 12/2016 | Donner et al. |
| 9,517,095 | B2 | 12/2016 | Vaidya |
| 9,526,548 | B2 | 12/2016 | Asfora |
| 9,554,909 | B2 | 1/2017 | Donner |
| 9,561,063 | B2 | 2/2017 | Reiley |

(56) References Cited

U.S. PATENT DOCUMENTS

| | | | |
|---|---|---|---|
| 9,566,100 | B2 | 2/2017 | Asfora |
| 9,603,613 | B2 | 3/2017 | Schoenefeld et al. |
| 9,603,644 | B2 | 3/2017 | Sweeney |
| D783,821 | S | 4/2017 | Folsom et al. |
| 9,622,783 | B2 | 4/2017 | Reiley et al. |
| 9,655,656 | B2 | 5/2017 | Whipple |
| 9,662,124 | B2 | 5/2017 | Assell et al. |
| 9,662,128 | B2 | 5/2017 | Reiley |
| 9,662,157 | B2 | 5/2017 | Schneider et al. |
| 9,662,158 | B2 | 5/2017 | Reiley |
| 9,675,394 | B2 | 6/2017 | Reiley |
| 9,743,969 | B2 | 8/2017 | Reiley |
| 9,757,154 | B2 | 9/2017 | Donner et al. |
| 9,763,695 | B2 | 9/2017 | Mirda |
| 9,763,802 | B2 | 9/2017 | Baynham |
| 9,775,648 | B2 | 10/2017 | Greenberg et al. |
| 9,788,866 | B2 | 10/2017 | Jackson |
| 9,808,292 | B2 | 11/2017 | Jackson |
| 9,808,298 | B2 | 11/2017 | Stroncek et al. |
| 9,808,299 | B2 | 11/2017 | Goel et al. |
| 9,808,337 | B2 | 11/2017 | Housman et al. |
| 9,820,789 | B2 | 11/2017 | Reiley |
| 9,826,986 | B2 | 11/2017 | Donner et al. |
| 9,839,448 | B2 | 12/2017 | Reckling et al. |
| 9,848,889 | B2 | 12/2017 | Taylor et al. |
| 9,848,892 | B2 | 12/2017 | Biedermann et al. |
| 9,883,874 | B1 | 2/2018 | Vestgaarden |
| 9,888,911 | B2 | 2/2018 | Siegal |
| 9,936,983 | B2 | 4/2018 | Mesiwala et al. |
| 9,949,776 | B2 | 4/2018 | Mobasser et al. |
| 9,949,843 | B2 | 4/2018 | Reiley et al. |
| 9,956,013 | B2 | 5/2018 | Reiley et al. |
| 9,993,276 | B2 | 6/2018 | Russell |
| 9,993,277 | B2 | 6/2018 | Krinke et al. |
| 9,999,449 | B2 | 6/2018 | Bonutti |
| 10,004,547 | B2 | 6/2018 | Reiley |
| 10,034,676 | B2 | 7/2018 | Donner |
| 10,058,430 | B2 | 8/2018 | Donner et al. |
| 10,064,670 | B2 | 9/2018 | Mootien et al. |
| 10,166,022 | B2 | 1/2019 | Early et al. |
| 10,166,033 | B2 | 1/2019 | Reiley et al. |
| 10,179,014 | B1 | 1/2019 | Menmuir et al. |
| 10,188,403 | B2 | 1/2019 | Mirochinik et al. |
| 10,188,432 | B2 | 1/2019 | Jackson et al. |
| 10,194,951 | B2 | 2/2019 | Jackson et al. |
| 10,194,962 | B2 | 2/2019 | Schneider et al. |
| 10,201,427 | B2 | 2/2019 | Mauldin et al. |
| 10,219,885 | B2 | 3/2019 | Mamo et al. |
| 10,245,044 | B2 | 4/2019 | Petersen |
| 10,245,076 | B2 | 4/2019 | Fitzpatrick |
| 10,245,087 | B2 | 4/2019 | Donner et al. |
| 10,258,380 | B2 | 4/2019 | Sinha |
| 10,258,394 | B2 | 4/2019 | Harshman et al. |
| 10,271,882 | B2 | 4/2019 | Biedermann et al. |
| 10,278,737 | B2 | 5/2019 | Smith |
| 10,292,778 | B2 | 5/2019 | Kostrzewski et al. |
| 10,314,631 | B2 | 6/2019 | Gonzalez Blohm et al. |
| 10,321,937 | B2 | 6/2019 | Cormier et al. |
| 10,321,945 | B2 | 6/2019 | Schifano et al. |
| 10,335,200 | B2 | 7/2019 | Jackson |
| 10,335,202 | B2 | 7/2019 | Ziolo et al. |
| 10,335,204 | B2 | 7/2019 | Matthis et al. |
| 10,335,206 | B2 | 7/2019 | Nichols et al. |
| 10,335,211 | B2 | 7/2019 | Chan et al. |
| 10,335,212 | B2 | 7/2019 | Paolino et al. |
| 10,335,216 | B2 | 7/2019 | Mari et al. |
| 10,342,586 | B2 | 7/2019 | Schneider |
| 10,349,983 | B2 | 7/2019 | Purcell et al. |
| 10,357,287 | B2 | 7/2019 | Schlaepfer et al. |
| 10,363,070 | B2 | 7/2019 | Jackson et al. |
| 10,363,140 | B2 | 7/2019 | Mauldin et al. |
| 10,363,143 | B2 | 7/2019 | Neubardt |
| 10,368,919 | B2 | 8/2019 | Pham et al. |
| 10,426,533 | B2 | 10/2019 | Mauldin et al. |
| 10,426,539 | B2 | 10/2019 | Schifano et al. |
| 10,433,880 | B2 | 10/2019 | Donner et al. |
| 10,441,319 | B2 | 10/2019 | Jackson et al. |
| 10,478,227 | B2 | 11/2019 | Leff et al. |
| 10,492,841 | B2 | 12/2019 | Hartdegen et al. |
| 10,492,921 | B2 | 12/2019 | Mcshane, III et al. |
| 10,517,734 | B2 | 12/2019 | Donner |
| 10,531,898 | B2 | 1/2020 | Boulot |
| 10,531,904 | B2 | 1/2020 | Kolb |
| 10,537,340 | B2 | 1/2020 | Mirochinik et al. |
| 10,555,758 | B2 | 2/2020 | Magee et al. |
| 10,588,676 | B2 | 3/2020 | Kang et al. |
| 10,588,677 | B2 | 3/2020 | McDonnell |
| 10,596,003 | B2 | 3/2020 | Donner et al. |
| 10,603,087 | B2 | 3/2020 | Brenzel et al. |
| 10,610,275 | B2 | 4/2020 | Brianza |
| 10,610,370 | B2 | 4/2020 | Baynham |
| 10,653,454 | B2 | 5/2020 | Frey et al. |
| 10,653,544 | B2 | 5/2020 | Forsell |
| 10,682,150 | B2 | 6/2020 | Stark |
| 10,682,437 | B2 | 6/2020 | Roth |
| 10,711,334 | B2 | 7/2020 | Patel et al. |
| 10,729,475 | B2 | 8/2020 | Childs |
| 10,729,482 | B2 | 8/2020 | Fantigrossi et al. |
| 10,743,995 | B2 | 8/2020 | Fallin et al. |
| 10,758,274 | B1 | 9/2020 | Bess et al. |
| 10,792,074 | B2 | 10/2020 | Jackson |
| 10,799,277 | B2 | 10/2020 | Kulper et al. |
| 10,799,367 | B2 | 10/2020 | Vrionis et al. |
| 10,842,634 | B2 | 11/2020 | Pasini et al. |
| D905,232 | S | 12/2020 | Schifano et al. |
| 10,898,333 | B2 | 1/2021 | Cordaro |
| 10,932,838 | B2 | 3/2021 | Mehl et al. |
| 10,959,758 | B2 | 3/2021 | Mesiwala et al. |
| 10,993,757 | B2 | 5/2021 | Schifano et al. |
| D922,568 | S | 6/2021 | Schifano et al. |
| 11,051,856 | B2 | 7/2021 | Jackson |
| 11,071,573 | B2 | 7/2021 | Schneider et al. |
| 11,116,519 | B2 | 9/2021 | Sand et al. |
| 11,147,591 | B2 | 10/2021 | Jackson |
| 11,147,597 | B2 | 10/2021 | Jackson |
| 11,147,688 | B2 | 10/2021 | Reckling et al. |
| 11,172,939 | B2 | 11/2021 | Donner et al. |
| 11,234,830 | B2 | 2/2022 | Mesiwala et al. |
| 11,266,767 | B2 | 3/2022 | Roth et al. |
| 11,284,798 | B2 | 3/2022 | Donner et al. |
| 11,284,887 | B2 | 3/2022 | Hartdegen et al. |
| 11,291,485 | B2 | 4/2022 | Mauldin et al. |
| D951,455 | S | 5/2022 | Ginn |
| 11,337,821 | B2 | 5/2022 | Mauldin et al. |
| 11,369,419 | B2 | 6/2022 | Mesiwala et al. |
| 11,446,069 | B2 | 9/2022 | Mauldin et al. |
| 11,471,286 | B2 | 10/2022 | Mauldin et al. |
| 11,478,287 | B2 | 10/2022 | Mauldin et al. |
| D972,137 | S | 12/2022 | Schifano et al. |
| 11,571,245 | B2 | 2/2023 | Stuart et al. |
| 11,607,251 | B2 | 3/2023 | Albert et al. |
| 11,607,256 | B1 | 3/2023 | Folsom et al. |
| 11,633,292 | B2 | 4/2023 | Reiley |
| 11,672,570 | B2 | 6/2023 | Stuart et al. |
| 11,672,664 | B2 | 6/2023 | Mauldin et al. |
| 11,678,997 | B2 | 6/2023 | Mesiwala et al. |
| 11,684,378 | B2 | 6/2023 | Reiley et al. |
| 11,752,011 | B2 | 9/2023 | Stuart et al. |
| 11,806,197 | B2 | 11/2023 | Frey et al. |
| 11,850,156 | B2 | 12/2023 | Mauldin et al. |
| 11,877,756 | B2 | 1/2024 | Sand et al. |
| 11,980,399 | B2 | 5/2024 | Mesiwala et al. |
| 11,986,397 | B2 | 5/2024 | Reiley |
| 12,004,961 | B2 | 6/2024 | Reiley |
| 12,023,079 | B2 | 7/2024 | Mauldin et al. |
| 12,042,402 | B2 | 7/2024 | Stuart et al. |
| 12,076,251 | B2 | 9/2024 | Mesiwala et al. |
| 12,083,026 | B2 | 9/2024 | Reckling et al. |
| 12,161,374 | B2 | 12/2024 | Schneider et al. |
| 12,167,877 | B2 | 12/2024 | Harshman et al. |
| 12,201,330 | B2 | 1/2025 | Stuart et al. |
| 12,245,795 | B2 | 3/2025 | Spangler et al. |
| 12,262,918 | B2 | 4/2025 | Yacoub et al. |
| 12,427,027 | B2 | 9/2025 | Ginn |

(56) References Cited

U.S. PATENT DOCUMENTS

| | | | |
|---|---|---|---|
| 12,465,499 | B2 | 11/2025 | Spann |
| 12,514,622 | B2 | 1/2026 | Larson |
| 2001/0012942 | A1 | 8/2001 | Estes et al. |
| 2001/0046518 | A1 | 11/2001 | Sawhney |
| 2001/0047207 | A1 | 11/2001 | Michelson |
| 2001/0049529 | A1 | 12/2001 | Cachia et al. |
| 2002/0019637 | A1 | 2/2002 | Frey et al. |
| 2002/0029043 | A1 | 3/2002 | Ahrens et al. |
| 2002/0038123 | A1 | 3/2002 | Visotsky et al. |
| 2002/0049497 | A1 | 4/2002 | Mason |
| 2002/0077641 | A1 | 6/2002 | Michelson |
| 2002/0082598 | A1 | 6/2002 | Teitelbaum |
| 2002/0120275 | A1 | 8/2002 | Schmieding et al. |
| 2002/0120335 | A1 | 8/2002 | Angelucci et al. |
| 2002/0128652 | A1 | 9/2002 | Ferree |
| 2002/0143334 | A1 | 10/2002 | von Hoffmann et al. |
| 2002/0143335 | A1 | 10/2002 | von Hoffmann et al. |
| 2002/0151903 | A1 | 10/2002 | Takel et al. |
| 2002/0169507 | A1 | 11/2002 | Malone |
| 2002/0183858 | A1 | 12/2002 | Contiliano et al. |
| 2002/0198527 | A1 | 12/2002 | Mückter |
| 2003/0018336 | A1 | 1/2003 | Vandewalle |
| 2003/0032961 | A1 | 2/2003 | Pelo et al. |
| 2003/0050642 | A1 | 3/2003 | Schmieding et al. |
| 2003/0065332 | A1 | 4/2003 | TenHuisen et al. |
| 2003/0074000 | A1 | 4/2003 | Roth et al. |
| 2003/0078660 | A1 | 4/2003 | Clifford et al. |
| 2003/0083668 | A1 | 5/2003 | Rogers et al. |
| 2003/0083688 | A1 | 5/2003 | Simonson |
| 2003/0088251 | A1 | 5/2003 | Braun et al. |
| 2003/0097131 | A1 | 5/2003 | Schon et al. |
| 2003/0139815 | A1 | 7/2003 | Grooms et al. |
| 2003/0181979 | A1 | 9/2003 | Ferree |
| 2003/0181982 | A1 | 9/2003 | Kuslich |
| 2003/0199983 | A1 | 10/2003 | Michelson |
| 2003/0229358 | A1 | 12/2003 | Errico et al. |
| 2003/0233146 | A1 | 12/2003 | Grinberg et al. |
| 2003/0233147 | A1 | 12/2003 | Nicholson et al. |
| 2004/0010315 | A1 | 1/2004 | Song |
| 2004/0024458 | A1 | 2/2004 | Senegas et al. |
| 2004/0034422 | A1 | 2/2004 | Errico et al. |
| 2004/0073216 | A1 | 4/2004 | Lieberman |
| 2004/0073314 | A1 | 4/2004 | White et al. |
| 2004/0082955 | A1 | 4/2004 | Zirkle |
| 2004/0087948 | A1 | 5/2004 | Suddaby |
| 2004/0097927 | A1 | 5/2004 | Yeung et al. |
| 2004/0106925 | A1 | 6/2004 | Culbert |
| 2004/0117022 | A1 | 6/2004 | Marnay et al. |
| 2004/0127990 | A1 | 7/2004 | Bartish, Jr. et al. |
| 2004/0138750 | A1 | 7/2004 | Mitchell |
| 2004/0138753 | A1 | 7/2004 | Ferree |
| 2004/0147929 | A1 | 7/2004 | Biedermann et al. |
| 2004/0158324 | A1 | 8/2004 | Lange |
| 2004/0176287 | A1 | 9/2004 | Harrison et al. |
| 2004/0176853 | A1 | 9/2004 | Sennett et al. |
| 2004/0181282 | A1 | 9/2004 | Zucherman et al. |
| 2004/0186572 | A1 | 9/2004 | Lange et al. |
| 2004/0210221 | A1 | 10/2004 | Kozak et al. |
| 2004/0210227 | A1 | 10/2004 | Trail et al. |
| 2004/0225360 | A1 | 11/2004 | Malone |
| 2004/0230305 | A1 | 11/2004 | Gorensek et al. |
| 2004/0260286 | A1 | 12/2004 | Ferree |
| 2004/0267369 | A1 | 12/2004 | Lyons et al. |
| 2005/0015059 | A1 | 1/2005 | Sweeney |
| 2005/0015146 | A1 | 1/2005 | Louis et al. |
| 2005/0033435 | A1 | 2/2005 | Belliard et al. |
| 2005/0037319 | A1 | 2/2005 | Bulard et al. |
| 2005/0049590 | A1 | 3/2005 | Alleyne et al. |
| 2005/0055023 | A1 | 3/2005 | Sohngen et al. |
| 2005/0070905 | A1 | 3/2005 | Donnelly et al. |
| 2005/0070907 | A1 | 3/2005 | Abernathie |
| 2005/0071004 | A1 | 3/2005 | Re et al. |
| 2005/0075641 | A1 | 4/2005 | Singhatat et al. |
| 2005/0080415 | A1 | 4/2005 | Keyer et al. |
| 2005/0107878 | A1 | 5/2005 | Conchy |
| 2005/0112397 | A1 | 5/2005 | Rolfe et al. |
| 2005/0113919 | A1 | 5/2005 | Cragg et al. |
| 2005/0124993 | A1 | 6/2005 | Chappuis |
| 2005/0131409 | A1 | 6/2005 | Chervitz et al. |
| 2005/0137605 | A1 | 6/2005 | Assell et al. |
| 2005/0143837 | A1 | 6/2005 | Ferree |
| 2005/0149192 | A1 | 7/2005 | Zucherman et al. |
| 2005/0158149 | A1 | 7/2005 | Panasik et al. |
| 2005/0159749 | A1 | 7/2005 | Levy et al. |
| 2005/0159812 | A1 | 7/2005 | Dinger et al. |
| 2005/0165398 | A1 | 7/2005 | Reiley |
| 2005/0192572 | A1 | 9/2005 | Abdelgany et al. |
| 2005/0216017 | A1 | 9/2005 | Fielding |
| 2005/0216082 | A1 | 9/2005 | Wilson et al. |
| 2005/0228384 | A1 | 10/2005 | Zucherman et al. |
| 2005/0228388 | A1 | 10/2005 | Brodke et al. |
| 2005/0246021 | A1 | 11/2005 | Ringeisen et al. |
| 2005/0251146 | A1 | 11/2005 | Martz et al. |
| 2005/0273101 | A1 | 12/2005 | Schumacher |
| 2005/0277940 | A1 | 12/2005 | Neff |
| 2006/0004396 | A1 | 1/2006 | Easley et al. |
| 2006/0025771 | A1 | 2/2006 | Jackson |
| 2006/0036247 | A1 | 2/2006 | Michelson |
| 2006/0036251 | A1 | 2/2006 | Reiley |
| 2006/0036252 | A1 | 2/2006 | Baynham et al. |
| 2006/0054171 | A1 | 3/2006 | Dall |
| 2006/0058793 | A1 | 3/2006 | Michelson |
| 2006/0058800 | A1 | 3/2006 | Ainsworth et al. |
| 2006/0062825 | A1 | 3/2006 | Maccecchini |
| 2006/0084986 | A1 | 4/2006 | Grinberg et al. |
| 2006/0089644 | A1 | 4/2006 | Felix |
| 2006/0089656 | A1 | 4/2006 | Allard et al. |
| 2006/0095038 | A1 | 5/2006 | Jackson |
| 2006/0111779 | A1 | 5/2006 | Petersen |
| 2006/0129247 | A1 | 6/2006 | Brown et al. |
| 2006/0142772 | A1 | 6/2006 | Ralph et al. |
| 2006/0161163 | A1 | 7/2006 | Shino |
| 2006/0178673 | A1 | 8/2006 | Curran |
| 2006/0195094 | A1 | 8/2006 | McGraw et al. |
| 2006/0217717 | A1 | 9/2006 | Whipple |
| 2006/0235387 | A1 | 10/2006 | Peterman |
| 2006/0241600 | A1 | 10/2006 | Ensign et al. |
| 2006/0241776 | A1 | 10/2006 | Brown et al. |
| 2006/0271054 | A1 | 11/2006 | Sucec et al. |
| 2006/0293662 | A1 | 12/2006 | Boyer, II et al. |
| 2007/0027544 | A1 | 2/2007 | McCord et al. |
| 2007/0038219 | A1 | 2/2007 | Matthis et al. |
| 2007/0049933 | A1 | 3/2007 | Ahn et al. |
| 2007/0066977 | A1 | 3/2007 | Assell et al. |
| 2007/0073295 | A1 | 3/2007 | Biederman et al. |
| 2007/0083265 | A1 | 4/2007 | Malone |
| 2007/0088362 | A1 | 4/2007 | Bonutti et al. |
| 2007/0093841 | A1 | 4/2007 | Hoogland |
| 2007/0093898 | A1 | 4/2007 | Schwab et al. |
| 2007/0106383 | A1 | 5/2007 | Abdou |
| 2007/0149976 | A1 | 6/2007 | Hale et al. |
| 2007/0156144 | A1 | 7/2007 | Ulrich et al. |
| 2007/0156241 | A1 | 7/2007 | Reiley et al. |
| 2007/0156246 | A1 | 7/2007 | Meswania et al. |
| 2007/0161985 | A1 | 7/2007 | Demakas et al. |
| 2007/0161989 | A1 | 7/2007 | Heinz et al. |
| 2007/0173820 | A1 | 7/2007 | Trieu |
| 2007/0219634 | A1 | 9/2007 | Greenhalgh et al. |
| 2007/0233080 | A1 | 10/2007 | Na et al. |
| 2007/0233146 | A1 | 10/2007 | Henniges et al. |
| 2007/0233247 | A1 | 10/2007 | Schwab |
| 2007/0250166 | A1 | 10/2007 | Mckay |
| 2007/0270833 | A1 | 11/2007 | Bonutti et al. |
| 2007/0270858 | A1 | 11/2007 | Trieu et al. |
| 2007/0270879 | A1 | 11/2007 | Isaza et al. |
| 2007/0276500 | A1 | 11/2007 | Zucherman et al. |
| 2007/0282443 | A1 | 12/2007 | Globerman et al. |
| 2008/0021454 | A1 | 1/2008 | Chao et al. |
| 2008/0021455 | A1 | 1/2008 | Chao et al. |
| 2008/0021456 | A1 | 1/2008 | Gupta et al. |
| 2008/0021461 | A1 | 1/2008 | Barker et al. |
| 2008/0021480 | A1 | 1/2008 | Chin et al. |
| 2008/0065093 | A1 | 3/2008 | Assell et al. |
| 2008/0065215 | A1 | 3/2008 | Reiley |

(56) References Cited

U.S. PATENT DOCUMENTS

2008/0071356 A1 3/2008 Greenhalgh et al.
2008/0109083 A1 5/2008 Van Hoeck et al.
2008/0125868 A1 5/2008 Branemark et al.
2008/0132901 A1 6/2008 Recoules-Arche et al.
2008/0140082 A1 6/2008 Erdem et al.
2008/0147079 A1 6/2008 Chin et al.
2008/0154314 A1 6/2008 McDevitt
2008/0154374 A1 6/2008 Labrom
2008/0161810 A1 7/2008 Melkent
2008/0161927 A1 7/2008 Savage et al.
2008/0183204 A1 7/2008 Greenhalgh et al.
2008/0234758 A1 9/2008 Fisher et al.
2008/0249579 A1 10/2008 Taylor
2008/0255562 A1 10/2008 Gil et al.
2008/0255618 A1 10/2008 Fisher et al.
2008/0255622 A1 10/2008 Mickiewicz et al.
2008/0255664 A1 10/2008 Hogendijk et al.
2008/0255666 A1 10/2008 Fisher et al.
2008/0255667 A1 10/2008 Horton
2008/0275454 A1 11/2008 Geibel
2008/0294202 A1 11/2008 Peterson et al.
2008/0306554 A1 12/2008 Mckinley
2009/0012529 A1 1/2009 Blain et al.
2009/0018660 A1 1/2009 Roush
2009/0024174 A1 1/2009 Stark
2009/0036927 A1 2/2009 Vestgaarden
2009/0037148 A1 2/2009 Lin et al.
2009/0043393 A1 2/2009 Duggal et al.
2009/0082810 A1 3/2009 Bhatnagar et al.
2009/0082869 A1 3/2009 Slemker et al.
2009/0099602 A1 4/2009 Aflatoon
2009/0099610 A1 4/2009 Johnson et al.
2009/0105770 A1 4/2009 Berrevooets et al.
2009/0118771 A1 5/2009 Gonzalez-Hernandez
2009/0131986 A1 5/2009 Lee et al.
2009/0138053 A1 5/2009 Assell et al.
2009/0157119 A1 6/2009 Hale
2009/0163920 A1 6/2009 Hochschuler et al.
2009/0171394 A1 7/2009 Adbou
2009/0187247 A1 7/2009 Metcalf, Jr. et al.
2009/0216238 A1 8/2009 Stark
2009/0270929 A1 10/2009 Suddaby
2009/0287254 A1 11/2009 Nayet et al.
2009/0312798 A1 12/2009 Varela
2009/0319043 A1 12/2009 McDevitt et al.
2009/0324678 A1 12/2009 Thorne et al.
2010/0003638 A1 1/2010 Collins et al.
2010/0022535 A1 1/2010 Lee et al.
2010/0076502 A1 3/2010 Guyer et al.
2010/0081107 A1 4/2010 Bagambisa et al.
2010/0094290 A1 4/2010 Vaidya
2010/0094295 A1 4/2010 Schnieders et al.
2010/0094420 A1 4/2010 Grohowski
2010/0106194 A1 4/2010 Bonutti et al.
2010/0106195 A1 4/2010 Serhan et al.
2010/0114174 A1 5/2010 Jones et al.
2010/0114317 A1 5/2010 Lambrecht et al.
2010/0131011 A1 5/2010 Stark
2010/0137990 A1 6/2010 Apatsidis et al.
2010/0145461 A1 6/2010 Landry et al.
2010/0160977 A1 6/2010 Gephart et al.
2010/0168798 A1 7/2010 Clineff
2010/0191292 A1 7/2010 DeMeo et al.
2010/0228301 A1 9/2010 Greenhalgh et al.
2010/0234890 A1 9/2010 Alamin et al.
2010/0262242 A1 10/2010 Chavatte et al.
2010/0268228 A1 10/2010 Petersen
2010/0280619 A1 11/2010 Yuan et al.
2010/0280622 A1 11/2010 McKinley
2010/0286778 A1 11/2010 Eisermann et al.
2010/0298889 A1 11/2010 Wilberg et al.
2010/0331851 A1 12/2010 Huene
2010/0331893 A1 12/2010 Geist et al.
2011/0009869 A1 1/2011 Marino et al.
2011/0009966 A1 1/2011 Michelson
2011/0022089 A1 1/2011 Assell et al.
2011/0029019 A1 2/2011 Ainsworth et al.
2011/0040338 A1 2/2011 Jackson
2011/0040362 A1 2/2011 Godara et al.
2011/0046737 A1 2/2011 Teisen
2011/0060373 A1 3/2011 Russell et al.
2011/0060375 A1 3/2011 Bonutti
2011/0066190 A1 3/2011 Schaller et al.
2011/0082551 A1 4/2011 Kraus
2011/0093020 A1 4/2011 Wu
2011/0098747 A1 4/2011 Donner et al.
2011/0098816 A1 4/2011 Jacob et al.
2011/0098817 A1 4/2011 Eckhardt et al.
2011/0106175 A1 5/2011 Rezach
2011/0153018 A1 6/2011 Walters et al.
2011/0160866 A1 6/2011 Laurence et al.
2011/0178561 A1 7/2011 Roh
2011/0184417 A1 7/2011 Kitch et al.
2011/0184518 A1 7/2011 Trieu
2011/0184519 A1 7/2011 Trieu
2011/0184520 A1 7/2011 Trieu
2011/0196372 A1 8/2011 Murase
2011/0213432 A1 9/2011 Geist et al.
2011/0230966 A1 9/2011 Trieu
2011/0238074 A1 9/2011 Ek
2011/0238124 A1 9/2011 Richelsoph
2011/0238181 A1 9/2011 Trieu
2011/0245930 A1 10/2011 Alley et al.
2011/0257755 A1 10/2011 Bellemere et al.
2011/0264229 A1 10/2011 Donner
2011/0276098 A1 11/2011 Biedermann et al.
2011/0295272 A1 12/2011 Assell et al.
2011/0295370 A1 12/2011 Suh et al.
2011/0313471 A1 12/2011 McLean et al.
2011/0313532 A1 12/2011 Hunt
2011/0319995 A1 12/2011 Voellmicke et al.
2012/0004730 A1 1/2012 Castro
2012/0035667 A1 2/2012 Van Nortwick et al.
2012/0083887 A1 4/2012 Purcell et al.
2012/0095560 A1 4/2012 Donner
2012/0165872 A1 6/2012 Alamin et al.
2012/0179256 A1 7/2012 Reiley
2012/0191191 A1 7/2012 Trieu
2012/0215315 A1 8/2012 Hochschuler et al.
2012/0226318 A1 9/2012 Wenger et al.
2012/0253398 A1 10/2012 Metcalf et al.
2012/0271424 A1 10/2012 Crawford
2012/0277866 A1 11/2012 Kalluri et al.
2012/0296428 A1 11/2012 Donner
2012/0323285 A1 12/2012 Assell et al.
2013/0018427 A1 1/2013 Pham et al.
2013/0030456 A1 1/2013 Assell et al.
2013/0030529 A1 1/2013 Hunt
2013/0035727 A1 2/2013 Datta
2013/0053852 A1 2/2013 Greenhalgh et al.
2013/0053854 A1 2/2013 Schoenefeld et al.
2013/0053902 A1 2/2013 Trudeau
2013/0053963 A1 2/2013 Davenport
2013/0072984 A1 3/2013 Robinson
2013/0085535 A1 4/2013 Greenhalgh et al.
2013/0096683 A1 4/2013 Kube
2013/0116793 A1 5/2013 Kloss
2013/0123850 A1 5/2013 Schoenefeld et al.
2013/0123935 A1 5/2013 Hunt et al.
2013/0131678 A1 5/2013 Dahners
2013/0144343 A1 6/2013 Arnett et al.
2013/0158609 A1 6/2013 Mikhail et al.
2013/0172736 A1 7/2013 Abdou
2013/0197590 A1 8/2013 Assell et al.
2013/0203088 A1 8/2013 Baerlecken et al.
2013/0218215 A1 8/2013 Ginn et al.
2013/0218282 A1 8/2013 Hunt
2013/0231746 A1 9/2013 Ginn et al.
2013/0237988 A1 9/2013 Mauldin
2013/0245703 A1 9/2013 Warren et al.
2013/0245763 A1 9/2013 Mauldin
2013/0253595 A1 9/2013 Zucherman et al.
2013/0267836 A1 10/2013 Mauldin et al.
2013/0267961 A1 10/2013 Mauldin et al.

(56) References Cited

U.S. PATENT DOCUMENTS

| | | | |
|---|---|---|---|
| 2013/0267989 | A1 | 10/2013 | Mauldin et al. |
| 2013/0274890 | A1 | 10/2013 | McKay |
| 2013/0325129 | A1 | 12/2013 | Huang |
| 2013/0338722 | A1 | 12/2013 | Yalizis |
| 2014/0012334 | A1 | 1/2014 | Armstrong et al. |
| 2014/0012340 | A1 | 1/2014 | Beck et al. |
| 2014/0012384 | A1 | 1/2014 | Kana et al. |
| 2014/0031934 | A1 | 1/2014 | Trieu |
| 2014/0031935 | A1 | 1/2014 | Donner et al. |
| 2014/0031938 | A1 | 1/2014 | Lechmann et al. |
| 2014/0031939 | A1 | 1/2014 | Wolfe et al. |
| 2014/0046380 | A1 | 2/2014 | Asfora |
| 2014/0074175 | A1 | 3/2014 | Ehler et al. |
| 2014/0088596 | A1 | 3/2014 | Assell et al. |
| 2014/0088707 | A1 | 3/2014 | Donner et al. |
| 2014/0094860 | A1 | 4/2014 | Reimels |
| 2014/0121776 | A1 | 5/2014 | Hunt |
| 2014/0135927 | A1 | 5/2014 | Pavlov et al. |
| 2014/0142700 | A1 | 5/2014 | Donner et al. |
| 2014/0172026 | A1 | 6/2014 | Biedermann et al. |
| 2014/0172027 | A1 | 6/2014 | Biedermann et al. |
| 2014/0200618 | A1 | 7/2014 | Donner et al. |
| 2014/0207240 | A1 | 7/2014 | Stoffman et al. |
| 2014/0257294 | A1 | 9/2014 | Gedet et al. |
| 2014/0257408 | A1 | 9/2014 | Trieu et al. |
| 2014/0276846 | A1 | 9/2014 | Mauldin et al. |
| 2014/0276851 | A1 | 9/2014 | Schneider et al. |
| 2014/0277139 | A1 | 9/2014 | Vrionis et al. |
| 2014/0277165 | A1 | 9/2014 | Katzman et al. |
| 2014/0277460 | A1 | 9/2014 | Schifano et al. |
| 2014/0277462 | A1 | 9/2014 | Yerby et al. |
| 2014/0277463 | A1 | 9/2014 | Yerby et al. |
| 2014/0288649 | A1 | 9/2014 | Hunt |
| 2014/0288650 | A1 | 9/2014 | Hunt |
| 2014/0296982 | A1 | 10/2014 | Cheng |
| 2014/0330382 | A1 | 11/2014 | Mauldin |
| 2014/0364917 | A1 | 12/2014 | Sandstrom et al. |
| 2015/0012051 | A1 | 1/2015 | Warren et al. |
| 2015/0039037 | A1 | 2/2015 | Donner et al. |
| 2015/0080951 | A1 | 3/2015 | Yeh |
| 2015/0080972 | A1 | 3/2015 | Chin et al. |
| 2015/0094765 | A1 | 4/2015 | Donner et al. |
| 2015/0112444 | A1 | 4/2015 | Aksu |
| 2015/0147397 | A1 | 5/2015 | Altschuler |
| 2015/0150683 | A1 | 6/2015 | Donner et al. |
| 2015/0173805 | A1 | 6/2015 | Donner et al. |
| 2015/0173904 | A1 | 6/2015 | Stark |
| 2015/0182268 | A1 | 7/2015 | Donner et al. |
| 2015/0190149 | A1 | 7/2015 | Assell et al. |
| 2015/0190187 | A1 | 7/2015 | Parent et al. |
| 2015/0198196 | A1 | 7/2015 | Horiuchi |
| 2015/0209094 | A1 | 7/2015 | Anderson |
| 2015/0216566 | A1 | 8/2015 | Mikhail et al. |
| 2015/0238203 | A1 | 8/2015 | Asfora |
| 2015/0250513 | A1 | 9/2015 | Sainte |
| 2015/0250611 | A1 | 9/2015 | Schifano et al. |
| 2015/0250612 | A1 | 9/2015 | Schifano et al. |
| 2015/0257892 | A1 | 9/2015 | Lechmann et al. |
| 2015/0313720 | A1 | 11/2015 | Lorio |
| 2015/0320450 | A1 | 11/2015 | Mootien et al. |
| 2015/0320451 | A1 | 11/2015 | Mootien et al. |
| 2015/0320469 | A1 | 11/2015 | Biedermann et al. |
| 2015/0342753 | A1 | 12/2015 | Donner et al. |
| 2016/0000488 | A1 | 1/2016 | Cross, III |
| 2016/0022429 | A1 | 1/2016 | Greenhalgh et al. |
| 2016/0095711 | A1 | 4/2016 | Castro |
| 2016/0095721 | A1 | 4/2016 | Schell et al. |
| 2016/0100870 | A1 | 4/2016 | Lavigne et al. |
| 2016/0106477 | A1 | 4/2016 | Hynes et al. |
| 2016/0106479 | A1 | 4/2016 | Hynes et al. |
| 2016/0120661 | A1 | 5/2016 | Schell et al. |
| 2016/0143671 | A1 | 5/2016 | Jimenez |
| 2016/0157897 | A1 | 6/2016 | Vaidya |
| 2016/0157908 | A1 | 6/2016 | Cawley et al. |
| 2016/0166291 | A1 | 6/2016 | Goel et al. |
| 2016/0166301 | A1 | 6/2016 | Papangelou et al. |
| 2016/0175113 | A1 | 6/2016 | Lins |
| 2016/0184103 | A1 | 6/2016 | Fonte et al. |
| 2016/0213487 | A1 | 7/2016 | Wilson et al. |
| 2016/0242820 | A1 | 8/2016 | Whipple et al. |
| 2016/0242912 | A1 | 8/2016 | Lindsey et al. |
| 2016/0249940 | A1 | 9/2016 | Stark |
| 2016/0287171 | A1 | 10/2016 | Sand et al. |
| 2016/0287301 | A1 | 10/2016 | Mehl et al. |
| 2016/0310188 | A1 | 10/2016 | Marino et al. |
| 2016/0310197 | A1 | 10/2016 | Black et al. |
| 2016/0324643 | A1 | 11/2016 | Donner et al. |
| 2016/0324656 | A1 | 11/2016 | Morris et al. |
| 2016/0374727 | A1 | 12/2016 | Greenhalgh et al. |
| 2017/0014235 | A1 | 1/2017 | Jones et al. |
| 2017/0020573 | A1 | 1/2017 | Cain et al. |
| 2017/0020585 | A1 | 1/2017 | Harshman et al. |
| 2017/0128214 | A1 | 5/2017 | Mayer |
| 2017/0135733 | A1 | 5/2017 | Donner et al. |
| 2017/0135737 | A1 | 5/2017 | Krause |
| 2017/0143513 | A1 | 5/2017 | Sandstrom et al. |
| 2017/0202511 | A1 | 7/2017 | Chang et al. |
| 2017/0209155 | A1 | 7/2017 | Petersen |
| 2017/0216036 | A1 | 8/2017 | Cordaro |
| 2017/0224393 | A1 | 8/2017 | Lavigne et al. |
| 2017/0246000 | A1 | 8/2017 | Pavlov et al. |
| 2017/0266007 | A1 | 9/2017 | Gelaude et al. |
| 2018/0036041 | A1 | 2/2018 | Pham et al. |
| 2018/0042735 | A1 | 2/2018 | Schell et al. |
| 2018/0228617 | A1 | 8/2018 | Srour et al. |
| 2018/0228621 | A1 | 8/2018 | Reiley et al. |
| 2018/0235643 | A1 | 8/2018 | Lins et al. |
| 2018/0256232 | A1 | 9/2018 | Russell |
| 2018/0296227 | A1 | 10/2018 | Meek et al. |
| 2018/0296347 | A1 | 10/2018 | Hamzey et al. |
| 2018/0360512 | A1 | 12/2018 | Mari |
| 2019/0133613 | A1 | 5/2019 | Reiley et al. |
| 2019/0247094 | A1 | 8/2019 | Yacoub et al. |
| 2019/0298528 | A1 | 10/2019 | Lindsey et al. |
| 2019/0298542 | A1 | 10/2019 | Kloss |
| 2019/0343640 | A1 | 11/2019 | Donner et al. |
| 2019/0343653 | A1 | 11/2019 | McKay |
| 2019/0388228 | A1 | 12/2019 | Donner et al. |
| 2020/0222195 | A1 | 7/2020 | Assell et al. |
| 2020/0246158 | A1 | 8/2020 | Bergey |
| 2020/0315647 | A1 | 10/2020 | Fojtik et al. |
| 2020/0315666 | A1 | 10/2020 | Nichols et al. |
| 2020/0345510 | A1 | 11/2020 | Reiley |
| 2021/0228360 | A1 | 7/2021 | Hunt et al. |
| 2021/0393408 | A1 | 12/2021 | Ginn |
| 2021/0393409 | A1 | 12/2021 | Ginn |
| 2022/0031474 | A1 | 2/2022 | Reckling et al. |
| 2022/0273447 | A1 | 9/2022 | Ginn |
| 2022/0273448 | A1 | 9/2022 | Ginn et al. |
| 2022/0280303 | A1 | 9/2022 | Mauldin et al. |
| 2022/0296377 | A1 | 9/2022 | Ginn et al. |
| 2022/0296378 | A1 | 9/2022 | Ginn |
| 2022/0304813 | A1 | 9/2022 | Ginn et al. |
| 2022/0304814 | A1 | 9/2022 | Ginn |
| 2022/0409381 | A1 | 12/2022 | Ginn |
| 2023/0000526 | A1 | 1/2023 | Follini et al. |
| 2023/0000630 | A1 | 1/2023 | Ginn et al. |
| 2023/0000631 | A1 | 1/2023 | Ginn et al. |
| 2023/0076180 | A1 | 3/2023 | Schifano et al. |
| 2023/0210667 | A1 | 7/2023 | Lindsey et al. |
| 2023/0270559 | A1 | 8/2023 | Mesiwala et al. |
| 2023/0293206 | A1 | 9/2023 | Mundis et al. |
| 2023/0329765 | A1 | 10/2023 | Lavigne et al. |
| 2023/0390078 | A1 | 12/2023 | Bergey et al. |
| 2023/0404762 | A1 | 12/2023 | Ginn et al. |
| 2024/0206885 | A1 | 6/2024 | Sand et al. |
| 2024/0225667 | A9 | 7/2024 | Reiley et al. |
| 2024/0238097 | A1 | 7/2024 | Mauldin et al. |
| 2024/0261107 | A1 | 8/2024 | Ginn et al. |
| 2024/0285410 | A1 | 8/2024 | Ginn et al. |
| 2024/0366401 | A1 | 11/2024 | Bergey |
| 2024/0374399 | A1 | 11/2024 | Stuart et al. |
| 2024/0390151 | A1 | 11/2024 | Ginn et al. |
| 2024/0398453 | A1 | 12/2024 | Mauldin et al. |

(56) References Cited

U.S. PATENT DOCUMENTS

| | | | |
|---|---|---|---|
| 2024/0407810 | A1 | 12/2024 | Mesiwala et al. |
| 2024/0415547 | A1 | 12/2024 | Wentz et al. |
| 2025/0009396 | A1 | 1/2025 | Vestgaarden |
| 2025/0099259 | A1 | 3/2025 | Cordaro |
| 2025/0177168 | A1 | 6/2025 | Reckling et al. |
| 2025/0366867 | A1 | 12/2025 | Mauldin et al. |
| 2026/0007419 | A1 | 1/2026 | Reiley et al. |
| 2026/0041567 | A1 | 2/2026 | Spann |
| 2026/0083481 | A1 | 3/2026 | Follini et al. |
| 2026/0083489 | A1 | 3/2026 | Black et al. |
| 2026/0090872 | A1 | 4/2026 | Stuart et al. |

FOREIGN PATENT DOCUMENTS

| | | | |
|---|---|---|---|
| CN | 1909848 | A | 2/2007 |
| CN | 101795632 | A | 8/2010 |
| CN | 102361601 | A | 2/2012 |
| CN | 102429716 | A | 5/2012 |
| CN | 104968283 | A | 10/2015 |
| CN | 109124748 | A | 6/2017 |
| DE | 102011001264 | A1 | 9/2012 |
| DE | 102012106336 | A1 | 1/2014 |
| EP | 1287796 | A1 | 3/2003 |
| EP | 2070481 | B1 | 2/2012 |
| EP | 2796104 | A1 | 10/2014 |
| EP | 2590576 | B1 | 10/2015 |
| EP | 2749238 | B1 | 3/2017 |
| EP | 2887899 | B1 | 8/2017 |
| EP | 2341852 | B1 | 8/2018 |
| EP | 2496162 | B1 | 10/2018 |
| EP | 3616634 | A1 | 3/2020 |
| EP | 2328495 | B1 | 7/2020 |
| EP | 2408389 | B1 | 4/2021 |
| JP | 59200642 | A | 11/1984 |
| JP | 05-176942 | A | 7/1993 |
| JP | 05184615 | A | 7/1993 |
| JP | 09149906 | A | 10/1997 |
| JP | 10-85231 | A | 4/1998 |
| JP | 11318931 | A | 11/1999 |
| JP | 2002509753 | A | 4/2002 |
| JP | 2003511198 | A | 3/2003 |
| JP | 2003533329 | A | 11/2003 |
| JP | 2003534046 | A | 11/2003 |
| JP | 2004121841 | | 4/2004 |
| JP | 2004512895 | | 4/2004 |
| JP | 2004516866 | | 6/2004 |
| JP | 2006506181 | | 2/2006 |
| JP | 2007535973 | A | 12/2007 |
| JP | 2008540036 | A | 11/2008 |
| JP | 2009000501 | A | 1/2009 |
| JP | 2009521990 | A | 6/2009 |
| JP | 2009533159 | A | 9/2009 |
| JP | 2010137016 | A | 6/2010 |
| JP | 2011041802 | A | 3/2011 |
| JP | 2011512939 | A | 4/2011 |
| JP | 2012030105 | A | 2/2012 |
| JP | 2014000402 | A | 1/2014 |
| JP | 2014147820 | A | 8/2014 |
| JP | 2015510506 | A | 4/2015 |
| JP | 2015171520 | A | 10/2015 |
| JP | 2015531282 | A | 11/2015 |
| JP | 2016515857 | A | 6/2016 |
| JP | 2017528251 | A | 9/2017 |
| JP | 2017533759 | A | 11/2017 |
| WO | WO97/31517 | A2 | 8/1997 |
| WO | WO01/17445 | A1 | 3/2001 |
| WO | WO02/38054 | | 5/2002 |
| WO | WO03/007839 | A2 | 1/2003 |
| WO | WO04/02344 | | 1/2004 |
| WO | WO2004/043277 | A1 | 5/2004 |
| WO | WO2005/009729 | A2 | 2/2005 |
| WO | WO2006/003316 | | 1/2006 |
| WO | WO2006/023793 | A2 | 3/2006 |
| WO | WO2006/074321 | A2 | 7/2006 |
| WO | WO2006/116850 | A1 | 11/2006 |
| WO | WO2008/153723 | A1 | 12/2008 |
| WO | WO2009/025884 | A2 | 2/2009 |
| WO | WO2009/029074 | A1 | 3/2009 |
| WO | WO2010/105196 | A1 | 9/2010 |
| WO | WO2011/010463 | A1 | 1/2011 |
| WO | WO2011/110865 | A2 | 9/2011 |
| WO | WO2011/124874 | A1 | 10/2011 |
| WO | WO2011/149557 | A1 | 12/2011 |
| WO | WO2012/015976 | A1 | 2/2012 |
| WO | WO2012/048008 | A1 | 4/2012 |
| WO | WO2013/000071 | A1 | 1/2013 |
| WO | WO2013/052807 | A2 | 4/2013 |
| WO | WO2013/119907 | A1 | 8/2013 |
| WO | WO2013/134678 | A1 | 9/2013 |
| WO | WO2014/145902 | A1 | 9/2014 |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

Eisner; New SI Joint Fusion System Cleared; Orthopedics This Week; Jun. 28, 2018; retreived from the internet <https://ryortho.com/breaking/new-si-joint-fusion-system-cleared/> on Sep. 8, 2022; 5 pages.

Khurana et al.; Percutaneous fusion of the sacroiliac joint with hollow modular anchorage screws, clinical and radiological outcome; J Bone Joint Surg; vol. 91-B, No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Third Party Observation; PCT/US2021/062337; Aug. 29, 2022; 6 pages.

Wise et al.; Minimally invasive sacroiliac arthrodesis, outcomes of a new technique; J Spinal Disord Tech; vol. 21; No. 8; pp. 579-584; Dec. 2008.

Mesiwala et al.; U.S. Appl. No. 18/716,090 entitled "Fusion cages and methods for sacro-iliac joint stabilization," filed Jun. 3, 2024.

Stuart et al.; U.S. Appl. No. 18/805,412 entitled "Pelvic stabilization implants, methods of use and manufacture," filed Aug. 14, 2024.

Reckling et al.; U.S. Appl. No. 18/809,229 entitled "Sacro-iliac joint stabilizing implants and methods of implantation," filed Aug. 19, 2024.

Mesiwala et al.; U.S. Appl. No. 18/810,211 entitled "Implants for spinal fixation and or fusion," filed Aug. 20, 2024.

Polly et al.; U.S. Appl. No. 19/024,752 entitled "Spine stabilization," filed Jan. 16, 2025.

Follini et al.; U.S. Appl. No. 19/078,206 entitled "Threaded bone implant and systems," filed Mar. 12, 2025.

Sand et al.; U.S. Appl. No. 18/951,349 entitled "Systems, devices, and methods for preparing bone to receive an implant," filed Nov. 18, 2024.

Sand et al.; U.S. Appl. No. 18/951,396 entitled "Sacroiliac joint stabilization, including implants, systems and methods of delivering implants," filed Nov. 18, 2024.

Anderson Jr. et al.; U.S. Appl. No. 18/870,896 entitled "Bi-lateral pelvic stabilization," filed Dec. 2, 2024.

Stuart et al.; U.S. Appl. No. 18/977,789 entitled "Bone stabilizing implants and methods of placement across si joints," filed Dec. 11, 2024.

Mesiwala et al.; U.S. Appl. No. 19/349,840 entitled "Fusion cages and methods for sacro-iliac joint stabilization," filed Oct. 3, 2025.

Lindsey et al.; U.S. Appl. No. 19/317,804, entitled Threaded implants and methods of use across bone segments, filed Sep. 3, 2025.

MATRIX IMPLANT

CROSS REFERENCE TO RELATED APPLICATIONS

This application is a continuation of U.S. patent application Ser. No. 17/443,388, filed Jul. 26, 2021, which is a continuation of U.S. patent application Ser. No. 16/263,971, filed Jan. 31, 2019, now U.S. Pat. No. 11,071,573, which is a continuation of U.S. patent application Ser. No. 15/593,208, filed May 11, 2017, now U.S. Pat. No. 10,194,962, which is a continuation of U.S. patent application Ser. No. 14/859,005, filed Sep. 18, 2015, now U.S. Pat. No. 9,662,157, which claims priority to U.S. Provisional Patent Application No. 62/052,379, filed Sep. 18, 2014, each of which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to bone implants that can be used to fuse two bone segments together.

BACKGROUND

Many types of hardware are available both for the fixation of bones that are fractured and for the fixation of bones that are to be fused (arthrodesed).

For example, the human hip girdle (see FIGS. 1 and 2) is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain patients.

To relieve pain generated from the SI-Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacro-iliac fusion. At the same time the cartilage has to be removed from the "synovial joint" portion of the SI-Joint. This requires a large incision to approach the damaged, subluxed, dislocated, fractured, or degenerated joint. The large incision and removal of tissue can cause significant trauma to the patient, resulting in pain and increasing the time to heal after surgery.

In addition, screw type implants tend to be susceptible to rotation and loosening, especially in joints that are subjected to torsional forces, such as the SI-Joint. Excessive movement of the implant after implantation may result in the failure of the implant to incorporate and fuse with the bone, which may result in the need to remove and replace the failed implant.

Consequently, it would be desirable to provide an implant for bone fusion or fixation that resists rotation, can be implanted using a minimally invasive procedure, and/or that can be used to rescue a failed implant.

SUMMARY OF THE DISCLOSURE

The present invention relates generally to bone implants that can be used to fuse two bone segments together.

In some embodiments, an implant for the fixation or fusion of the SI-Joint is provided. The implant can include an elongate body having a longitudinal axis and a rectilinear cross-sectional profile transverse to the longitudinal axis, the elongate body having a proximal end and a distal end. The elongate body can include a plurality of apex struts aligned with the longitudinal axis and extending between the proximal end and the distal end of the elongate body; a plurality of support struts that extend from one apex strut to another apex strut to form a matrix structure; and a first guide pin receptacle located along the longitudinal axis of the elongate body.

In some embodiments, the rectilinear cross-sectional profile is triangular.

In some embodiments, the rectilinear cross-sectional profile is rectangular or square.

In some embodiments, the elongate body is curved along the longitudinal axis from the proximal end to the distal end of the elongate body. In some embodiments, the elongate body has a curvature between about 5 and 45 degrees.

In some embodiments, the elongate body has a curvature between about 15 and 30 degrees.

In some embodiments, the guide pin receptacle has a circular opening adapted to securely receive a guide pin.

In some embodiments, the elongate body is coated with a titanium plasma spray.

In some embodiments, the elongate body is coated with hydroxyapatite.

In some embodiments, the elongate body is made of metal.

In some embodiments, the metal is titanium.

In some embodiments, the metal comprises a lattice structure.

In some embodiments, the lattice structure is cubic.

In some embodiments, the lattice structure is hexagonal.

In some embodiments, the lattice structure comprises a plurality of beams with a diameter between about 100 to 1000 microns.

In some embodiments, the elongate body is made of a ceramic material.

In some embodiments, the elongate body is mode of a plastic material.

In some embodiments, the elongate body has a porous outer surface.

In some embodiments, all struts are covered in a porous surface.

In some embodiments, all struts are preferentially covered in a porous surface.

In some embodiments, the porous outer surface has a pore size between about 100 to 1000 microns.

In some embodiments, the thickness of the apex struts and the support struts is between about 1 to 5 mm.

In some embodiments, the first guide pin receptacle is located at the distal end of the elongate body.

In some embodiments, the first guide pin receptacle is located at the proximal end of the elongate body.

In some embodiments, the first guide pin receptacle is located at the distal end of the elongate body and a second guide pin receptacle is located at the proximal end of the body.

In some embodiments, the implant can further include a continuous cannula extending between the first guide pin receptacle and the second guide pin receptacle.

In some embodiments, a third guide pin receptacle is located between the first guide pin receptacle and the second guide pin receptacle.

In some embodiments, a plurality of pin receptacles are located between the first guide pin receptacle and the second guide pin receptacle.

In some embodiments, a modular implant for the fixation or fusion of the SI-Joint is provided. The modular implant includes a distal portion comprising a frame, the frame joined to a distal guide pin receptacle and to a plurality of transverse support struts arranged in a rectilinear configuration; a proximal portion comprising a frame joined to a proximal guide pin receptacle and to a plurality of transverse support struts arranged in a rectilinear configuration; and at least one repeating internal portion. The at least one repeating internal portion comprises a plurality of apex struts joined together by oblique support struts arranged in an oblique configuration between the apex struts, a plurality of transverse support struts arranged perpendicularly to the apex struts, the plurality of transverse support struts arranged in a rectilinear configuration at both a proximal end and a distal end of the repeating internal portion, and an internal guide pin receptacle secured to the support struts and aligned with both the distal guide pin receptacle and the proximal guide pin receptacle; wherein the at least one internal repeating portion is positioned between the distal portion and the proximal portion such that the transverse support struts of the distal portion are aligned with a first set of transverse support struts of the repeating internal portion and the transverse support struts of the proximal portion are aligned with the a second set of transverse support struts of the repeating internal portion.

In some embodiments, the oblique supports struts are arranged in an "X" configuration. In some embodiments, the oblique supports struts are arranged in a non-overlapping diagonal configuration.

In some embodiments, the apex and support struts are arranged and spaced to accept bone graft material from the outer surface toward the center of the implant.

In some embodiments, the graft material is autograft.

In some embodiments, the graft material is allograft.

In some embodiments, the graft material is bone morphogenetic protein.

In some embodiments, the implant does not have any struts that extend from the outer surface toward the center of the implant, thereby forming a cavity for receiving a graft material and/or guide pin.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
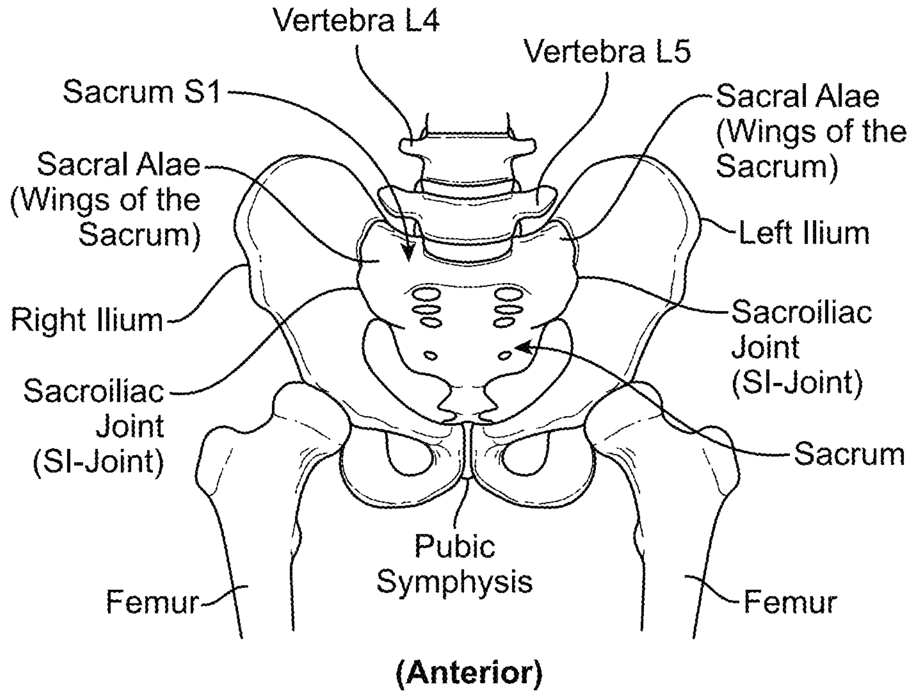
FIGS. 1 and 2 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 2:
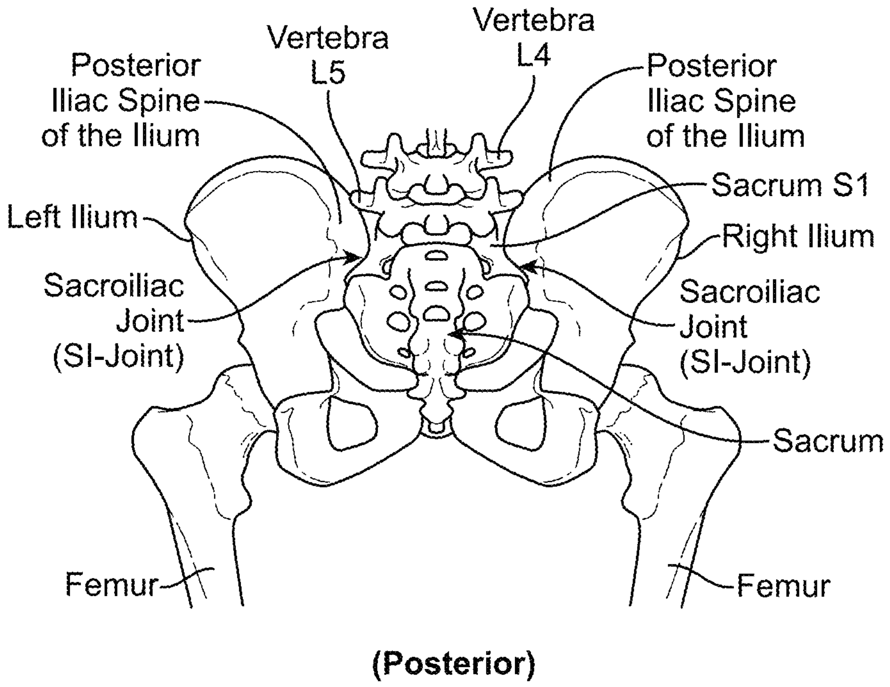
Figure 3:
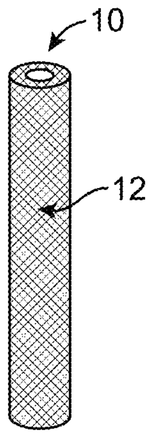
FIGS. 3 and 4 are embodiments of various straight implants that can be used for the fusion or fixation of a joint or two bone segments.
Figure 4:
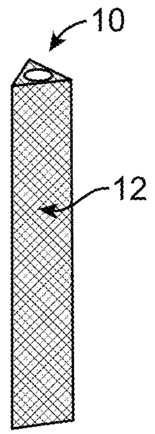

FIG. 3 and FIG. 4 illustrate straight implants 10 with a solid elongate body 12 that can be used for the fixation or fusion of two bone segments. The implant 10 shown in FIG. 3 is cylindrical and can optionally have screw threads along the exterior of the implant body. As mentioned above, cylindrical screw type implants can suffer from excessive rotation. One solution to this problem is the implant 10 in FIG. 4, which has a non-cylindrical cross-sectional area. For example, as shown, the implant 10 can have a triangular cross-sectional area, although other rectilinear cross-sectional profiles may be used as well, including rectangular, hexagonal and the like. Non-cylindrical implants need not have a strict rectilinear cross-sectional profile in order to resist rotation. A cross-sectional area that is non-circular will generally suffice. For example, a tear drop shaped cross-sectional area, or a cross-sectional area with at least one apex, can resist rotation. Other non-circular cross-sectional geometries that may not have a rectilinear component can also work, such as oval cross-sections.

Figure 5:
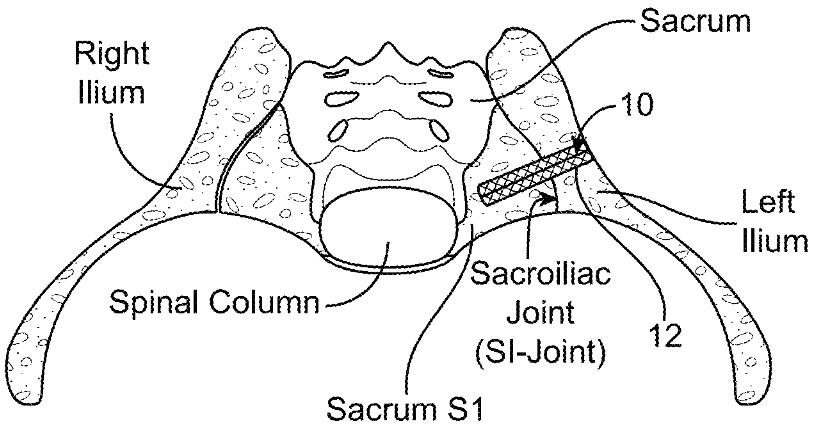
FIG. 5 illustrates an axial section view of the SI-Joint with an implant for the fixation of the SI-Joint using a lateral approach that goes laterally through the ilium, the SI-Joint, and into the sacrum 51.
Figure 6:
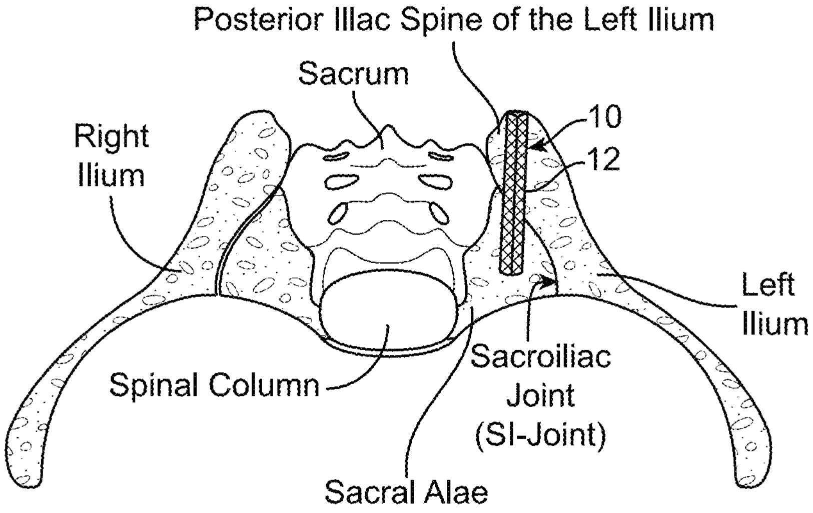
FIG. 6 illustrates an axial section view of the SI-Joint with an implant for the fixation of the SI-Joint using a postero-lateral approach entering from the posterior iliac spine of the ilium, angling through the SI-Joint, and terminating in the sacral alae.

FIG. 5 illustrates insertion of the implant 10 of FIG. 3 or FIG. 4 across the SI-Joint using a lateral approach that goes laterally through the ilium, across the SI-Joint, and into the sacrum. FIG. 6 illustrates insertion of the same implant across the SI-Joint using a postero-lateral approach entering from the posterior iliac spine of the ilium, angling through the SI-Joint, and terminating in the sacral alae. Many of the implants described herein can be inserted across the SI-Joint in a similar manner.

Matrix Implant

In some embodiments, it may be desirable to provide an implant with an open frame structure that can be packed with bone graft material and/or a biologic aid, while providing enough strength to facilitate the fusion of a joint or two bone segments without implant bending or failure.

One way to provide an open frame structure is to construct the elongate body 12 of the implant 10 using a matrix structure, as illustrated in FIGS. 7A-7C and 7G-7I. In some embodiments, each face or side of the elongate body 12 can be constructed using a matrix structure. The implant 10 can have a rectilinear overall cross-sectional profile transverse to a longitudinal axis that extends through the length of the elongate body 12. Each corner or apex of elongate body 12 can be formed with an apex strut 14 that extends between the proximal end 16 and the distal end 18 of the elongate body 12. An implant with a triangular overall cross-sectional profile has three apex struts, while an implant with a square or rectangular overall cross-sectional profile has four apex struts, and so on. To form the faces of the implant, support struts 20 can be arranged in various matrix structures.

Figure 7A:
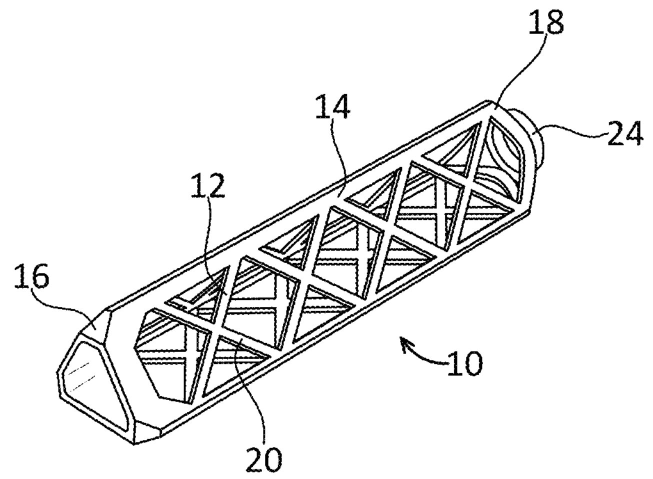
FIGS. 7A-7C illustrate various embodiments of implants having a matrix structure formed from a plurality of struts.

For example, FIG. 7A illustrates one embodiment of a matrix structure where the support struts 20 extend diagonally between two apex struts 14 and cross each other in an "X" configuration such that the support struts 20 define triangular and square openings. Additional transverse support struts that extend between two apex struts at a right angle to both apex struts can also be added. The transverse support struts can be positioned between the "X" support struts and/or can be positioned to cross the middle or intersection of the "X" support struts.

Figure 7B:
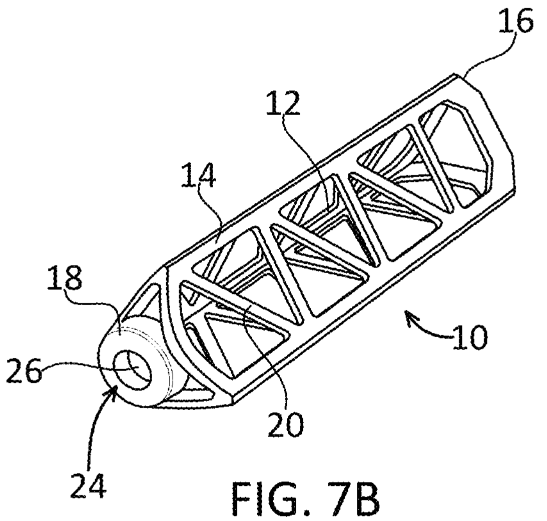

FIG. 7B illustrates another embodiment of a matrix structure where the support struts 20 are arranged in an alternating diagonal and transverse pattern. In this embodiment, the diagonal support struts on one face of the implant are all angled in the same direction such that the diagonal support struts are parallel to each other. The support struts 20 define triangular openings.

Figure 7C:
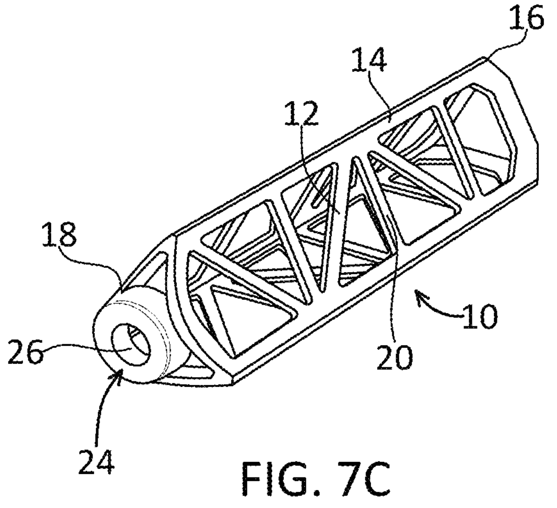

FIG. 7C illustrates yet another embodiment of a matrix structure where the support struts 20 are arranged in an alternating diagonal and transverse pattern. In this embodiment, the diagonal support struts are angled in an alternating pattern such that the diagonal support struts are oriented about 90 degrees to one another to form a zigzag pattern. The support struts 20 also define triangular openings.

The various matrix structures can provide different levels of resistance to various forces that the implant will be subjected to, including compressive, tensile, shear, bending, and torsional forces.

Figure 8:
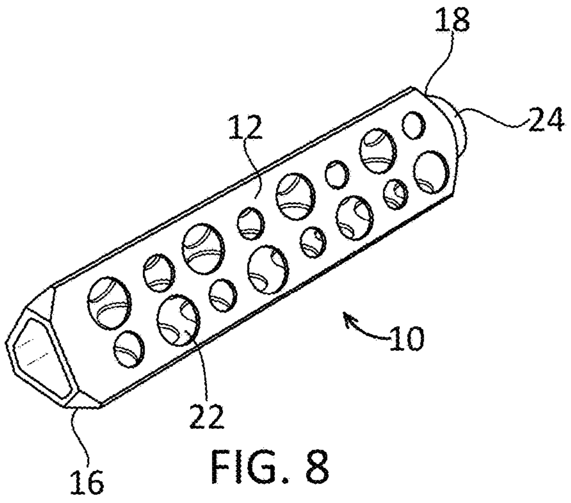
FIG. 8 illustrates an embodiment of a fenestrated implant.

FIG. 8 illustrates an alternative to using a matrix structure to provide openings. The implant 10 can have an elongate body 12 with fenestrations 22. The fenestrations 22 can be circular as shown, and can be of different sizes in, for example, an alternating pattern of large and small fenestrations. The fenestrations 22 can alternatively be rectilinear in shape, such as triangular, square, rectangular, and the like, or curvilinear, such as elliptical, oval, or circular.

In some embodiments, the fenestrations 22 can be triangular, square, rectangular or combinations of the above and can be arranged to form a matrix structure. In other words, the openings in FIGS. 7A-7B defined by the support struts 20 can be considered fenestrations 22.

Figure 7D:
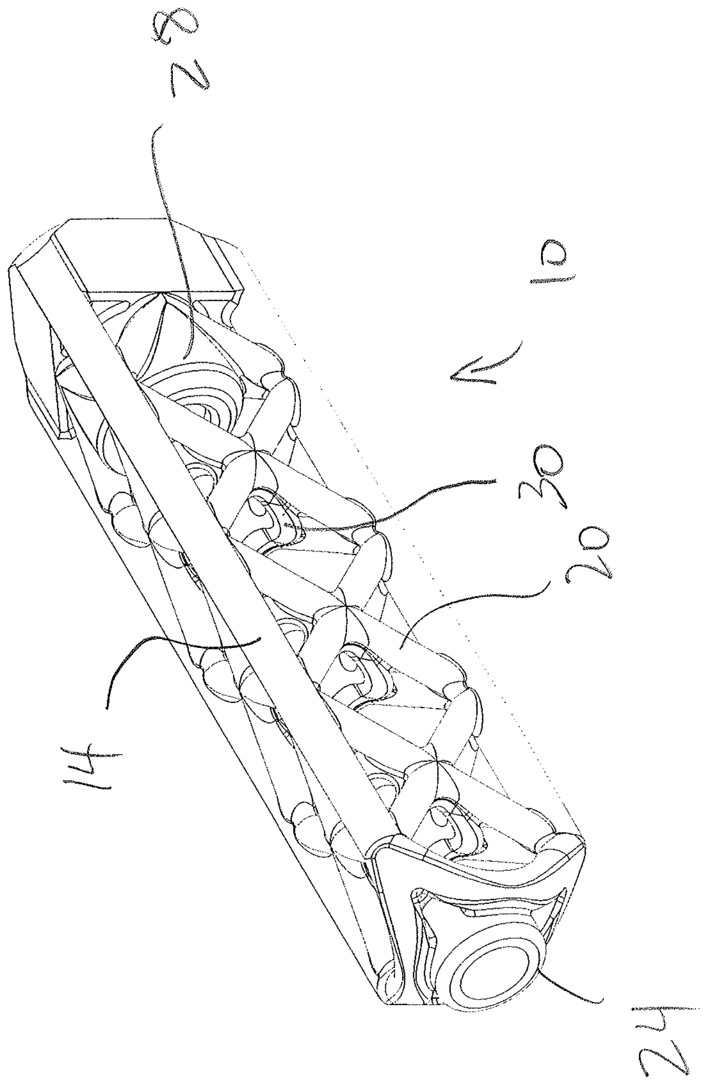
FIGS. 7D-7F illustrate various embodiments of implants having a matrix structure with a plurality of pin receptacles.
Figure 7E:
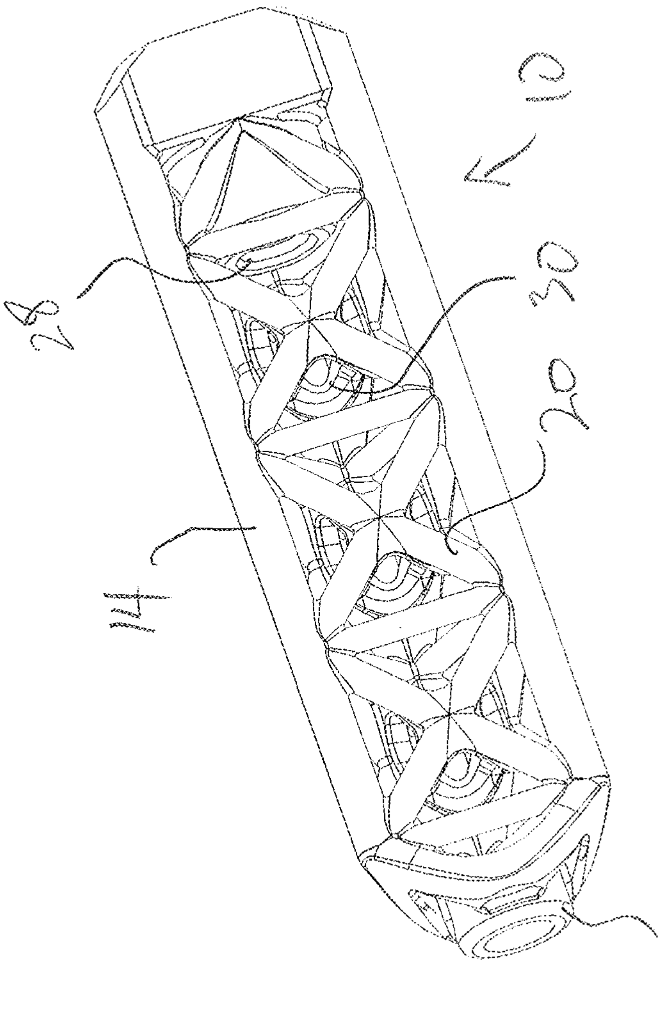
Figure 7F:
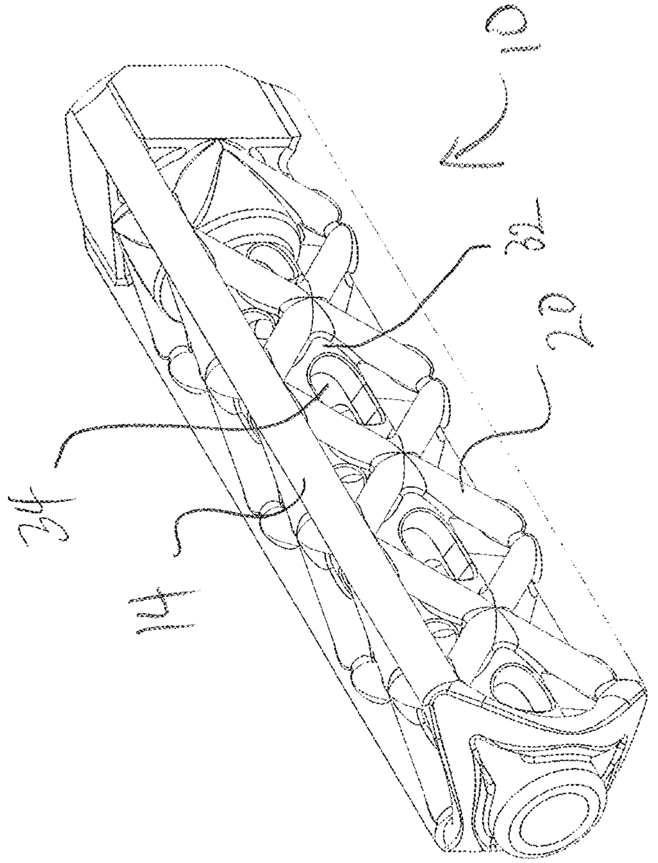
Figure 7G:
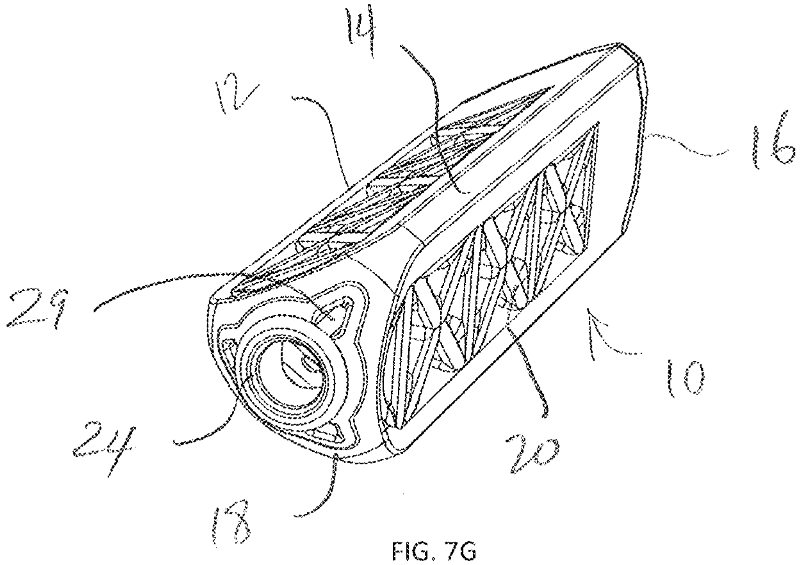
FIGS. 7G-7I illustrate another embodiment of an implant having a matrix structure from various angles and cross-sections.
Figure 7H:
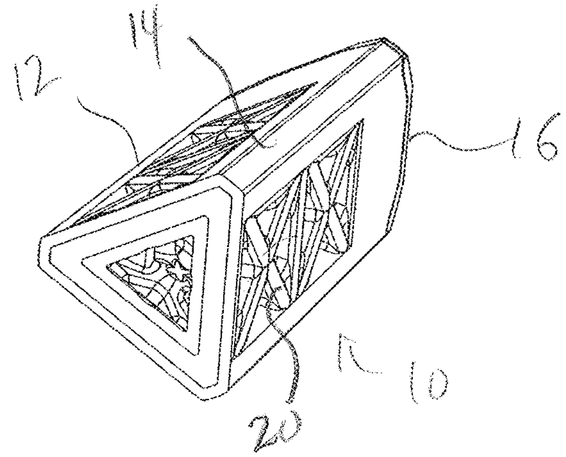
Figure 7I:
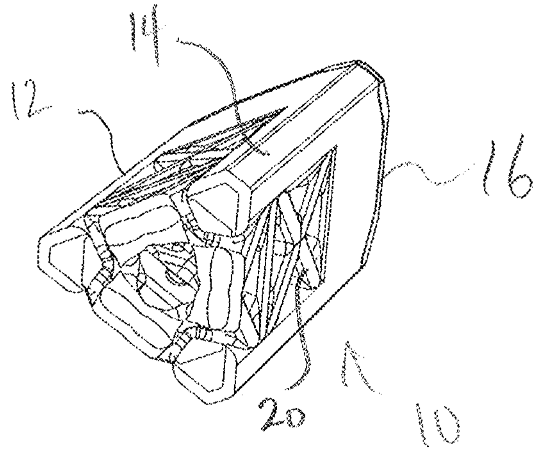

The walls of elongate body 12 can be planar and, as described above, can be formed from support struts 20 and/or fenestrations 22, as shown in FIGS. 7G-7I, for example. Using planar walls to form the elongate body 12 can result in a hollow cavity with the same or similar cross-sectional profile as the overall implant. For example, an implant with a triangular overall cross-sectional profile can also have a cavity with a triangular cross-sectional profile. The thickness of the walls and the apex struts and support struts can be between about 1 mm and 5 mm, or between about 1 and 3 mm. In addition, the distal ends of the walls can be tapered.

To facilitate the use of a traditional guide pin with these implants, the distal end of the implant can include a distal guide pin receptacle 24 with an opening 26 that is sized and shaped to receive a guide pin, as shown in FIGS. 7A-8. For example, the opening 26 can be circular to receive a typical guide pin. In some embodiments, the proximal end can additionally or alternatively have a proximal guide pin receptacle with an opening sized and shaped to receive a guide pin. In some embodiments, a continuous cannula can extend from the proximal guide pin receptacle to the distal guide pin receptacle. In some embodiments, multiple individual and co-linear guide pin receptacles can be present within the implant body between the proximal guide pin receptacle and the distal guide pin receptacle.

For example, FIG. 7D illustrates another embodiment of a matrix structure, similar to the embodiment shown in FIG. 7A, with support struts 20 that extend diagonally between apex struts 14 in an "X" configuration. However, in this embodiment, the implant 10 has a proximal guide pin receptacle 28 located at the proximal end of the implant, a distal guide pin receptacle 24 located at the distal end of the implant, and a plurality of internal guide pin receptacles 30 also located along the longitudinal axis of the implant. The internal guide pin receptacles 30 can be attached to the support struts 20 and/or apex struts 14. As shown, the internal guide pin receptacles 30 are attached at the intersection points of the "X" shaped support struts 20. In addition to receiving the guide pin, the internal guide pin receptacles 30 can provide additional support and bracing to the matrix structure.

FIG. 7E illustrates another embodiment of a matrix structure that is similar to the embodiment shown in FIG. 7D. Both embodiments have "X" shaped support struts 20 and a plurality of internal guide pin receptacles 30. However, this embodiment has additional support struts 20 that extend transversely between the apex struts 14 at right angles. The transverse support struts can be positioned between the "X" shaped support struts as shown, or can be integrated into the "X" shaped support struts. The transverse support struts can provide additional support and bracing to the matrix structure.

FIG. 7F illustrates another embodiment of a matrix structure that is similar to the embodiment shown in FIG. 7D. However, instead of having a plurality of guide pin receptacles, the implant 10 has a single guide pin receptacle 32 that extends from the proximal end to the distal end of the implant. This guide pin receptacle 32 can be a tube or cannula that can be attached to the support struts 20. In some embodiments, the tube or cannula can also have a plurality of fenestrations 34. In some embodiments, the fenestrations 34 can be positioned along the openings of the support struts, which allows the tube to support the support struts 20 while fenestrations promote bony ingrowth and allow the introduction of bone graft material through the implant.

FIGS. 7G-7I illustrates another embodiment of a matrix structure that is similar to the embodiment shown in FIG. 7E. This embodiment also has "X" shaped support struts 20 and additional support struts 20 that extend transversely between the apex struts 14 at right angles. One difference between this embodiment and the embodiment illustrated in FIG. 7E is that the support struts 20 and apex struts 14 in this embodiment have generally rectilinear cross-sectional profiles while the embodiment disclosed in FIG. 7E has generally circular support struts 20 and apex struts 14. In some embodiments, the apex struts 14 can be chamfered to remove sharp edges and the apices of the implant. In addition, this embodiment can have a distal guide pin receptacle 24 and a proximal guide pin receptacle, but unlike some of the embodiments described above, can lack internal guide pin receptacles. The guide pin can instead be supported internally by the inherent cross-sectional geometry of the apex struts and/or support struts. Any of the embodiments herein can have rectilinear, circular, or a combination of the two cross-sectional profiles. The use of the rectilinear struts may allow for the fabrication of the matrix implant by laser cutting a walled structure, while tubular struts may be welded together. A laser cut structure may be structurally stronger than a welded structure, which is important for supporting the large loads applied to the implant after implantation. The distal end 18 of the implant 10 can also have one or more openings 29 that allow graft material to be injected distally through the implant after implantation. In addition, any of the embodiments described herein can optionally have the internal guide pin receptacles, or omit the internal guide pin receptacles. FIG. 7H illustrates a cross-sectional view taken through the transverse struts, while FIG. 7I illustrates a cross-sectional view taken through the “X” shaped support struts.

Figure 9A:
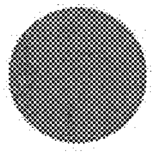
FIGS. 9A-9D illustrate various cross-sectional profiles of the implant microstructure, which can be formed with beam microstructures of varying geometries.
Figure 9B:
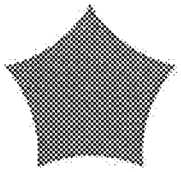
Figure 9C:
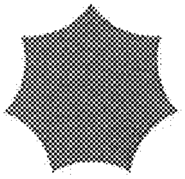
Figure 9D:
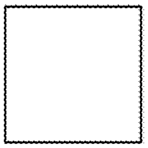

The implant, including the apex struts and/or support struts of the matrix as well as the beams that form the microstructure, can have a variety of shapes. For example, the beams and/or struts can have a cross-section that is rectilinear, curvilinear, or combinations of the two, as illustrated in FIGS. 9A-9D. For example, the beams and/or struts can have a circular cross-section as shown in FIG. 9A, or a curvilinear cross-section as shown in FIGS. 9B and 9C, or a square or rectangular cross section as shown in FIG. 9D. It should be understood that the corners and edges of the beams and/or struts can be rounded off if desired.

Figure 10A:
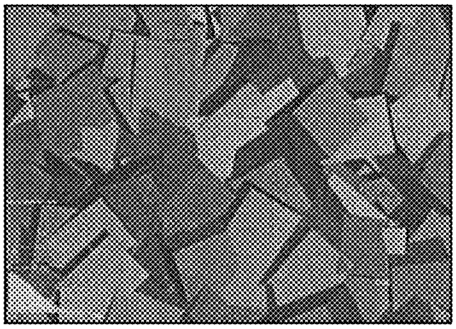
FIGS. 10A-10C illustrate various alternative beam microstructures.
Figure 10B:
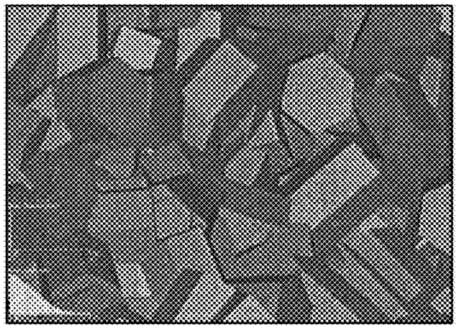
Figure 10C:
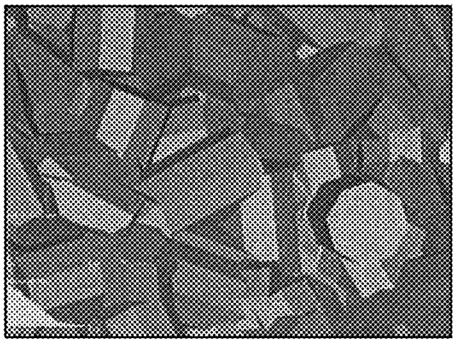
Figure 11A:
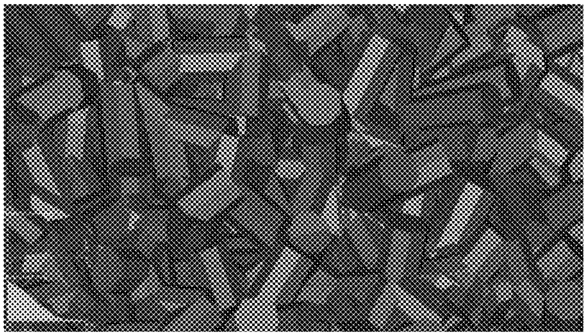
FIGS. 11A-11D illustrate various sizes for the beams that form the implant microstructure.
Figure 11B:
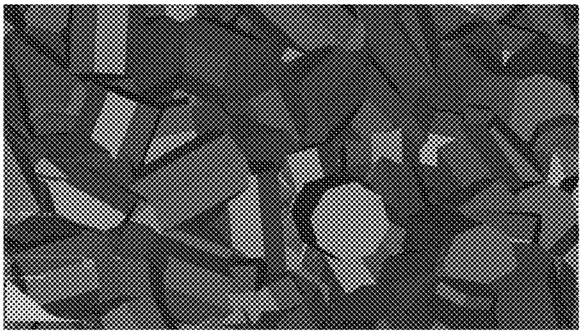
Figure 11C:
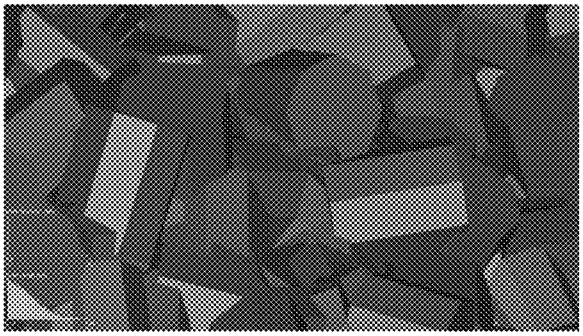
Figure 11D:
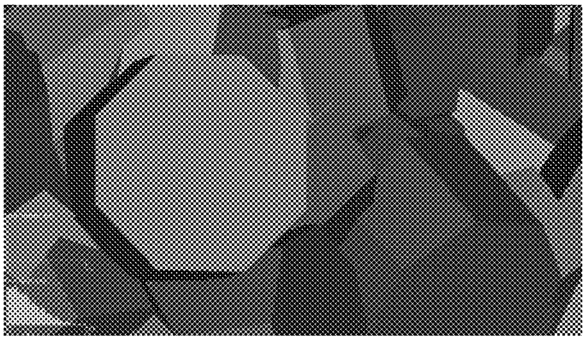

The implant can be made of a variety of materials. For example, the implant can be made of a metal or metal alloy, such as titanium or steel, or a nonmetallic material such as ceramic or polymer. In some embodiments, the implant material can have a certain lattice microstructure formed from the beam microparticles. For example, the lattice microstructure of the apex strut, support struts and other parts of the implant can result in a rough or smooth surface texture, depending on the surface finishing techniques used, such as polishing or application of a metal plasma spray, and the size and shape of the beams that form the lattice microstructure. For example, FIGS. 10A-10C illustrate various beam microstructures that can form the lattice microstructure. FIG. 10A illustrates a cubic beam structure, while FIG. 10B illustrates a hexagonal beam structure, and FIG. 10C illustrates an octagonal beam structure. Other beam structures include tetragonal, rhombohedral, orthorhombic, monoclinic, and triclinic. FIGS. 11A-11D illustrate that the beams can have various sizes. For example, FIGS. 11A-11D illustrate beams having a diameter of about 100, 200 microns, 350 microns, 500 microns, and 1000 microns. In other embodiments, the size of the beam can vary between 50 microns to 5000 microns.

The matrix implant can be manufactured using a variety of techniques. For example, the matrix implant can be 3-D printed using a rapid prototyping technique involving additive manufacturing, such as described in U.S. Patent Publication No. 2010/0161061, which is herein incorporated by reference in its entirety for all purposes. The 3-D printed matrix implant can be made of a metal, polymer, or ceramic material. For example, a metal powder such as titanium powder can be fused together to form the implant structure. Other techniques include cutting out the fenestrations or openings, using a laser for example, to form the apex struts and support struts, or using electric discharge machining (EDM) to create the matrixes or fenestrations.

3-D printing allows the porosity of the implant to be controlled. For example, the implant can have a volume porosity between about 30 and 70 percent, with an average pore size between 100 and 1000 microns. The pores can be largely interconnected, largely unconnected, or a mix of interconnected and unconnected pores. In some embodiments, the pores can be located throughout the material of the implant, including the apex struts and support struts, and on all or some of the strut surfaces, including the inner and outer implant surfaces. For example, the fusion of the beam microparticles to form the struts can result in a porous, semi-porous, or nonporous structure, depending on the degree of fusion between the beam microparticles. In other embodiments, the pores can be located in a porous coating that can be applied onto the implant. For example, a porous coating can be applied using a titanium plasma spray process, or another metal plasma spray process. The coating can be applied to the outer surfaces of the implant, the interior surfaces of the implant, or both the outer and interior surfaces of the implant. For example, the coating could be preferentially applied to the outer surface of a matrixed implant to provide bony ingrowth and ongrowth, and not applied to the inner portion of the implant to maximize bony through-growth within the implant. Also, the coating can be applied preferentially from proximal to distal, or vice versa. The thickness of a porous coating can be between about 500 and 1,500 microns. In addition or alternatively to the porous metal coating, a hydroxyapatite coating can also be applied to the implant. In some embodiments, the porosity can be varied along the length of the implant. In some embodiments, the thickness of the coating can be varied along the length of the implant. In some embodiments, the thickness of the coating applied to the outer surface can be different than the thickness of the inner coating. For example, the outer coating may be greater than the inner coating in some embodiments. In other embodiments, the thickness of the inner and outer coatings can be the same.

Figure 12:
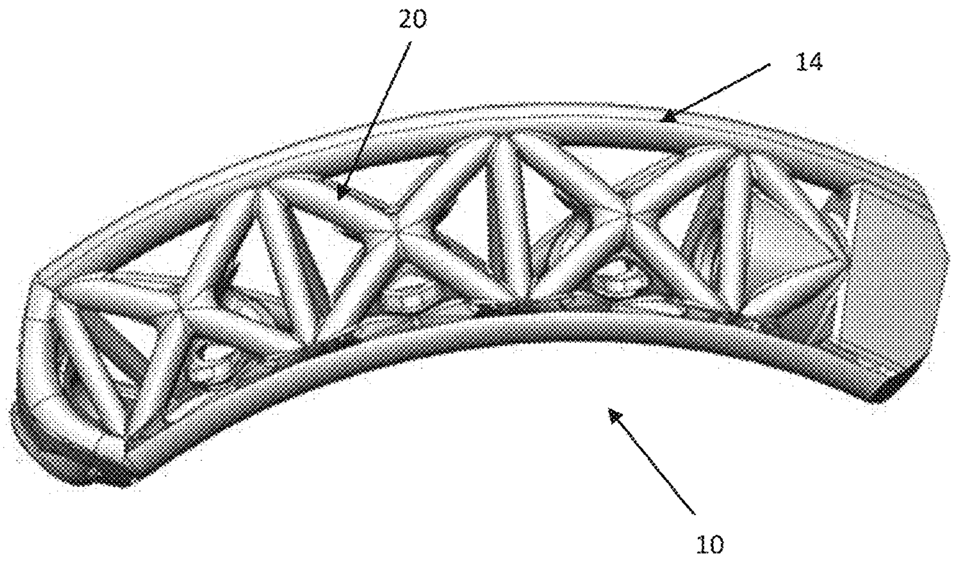
FIG. 12 illustrates an embodiment of a curved matrix implant.

In some embodiments, as illustrated in FIG. 12, the apex struts 14 can be curved from the proximal end to the distal end of the apex strut 14, thereby resulting in a curved matrix implant 10 similar to the curved implants described in U.S. Provisional Application No. 62/052,318, filed Sep. 18, 2014 and entitled “IMPLANTS FOR BONE FIXATION OR FUSION,” which is herein incorporated by reference in its entirety for all purposes.

Figure 13:
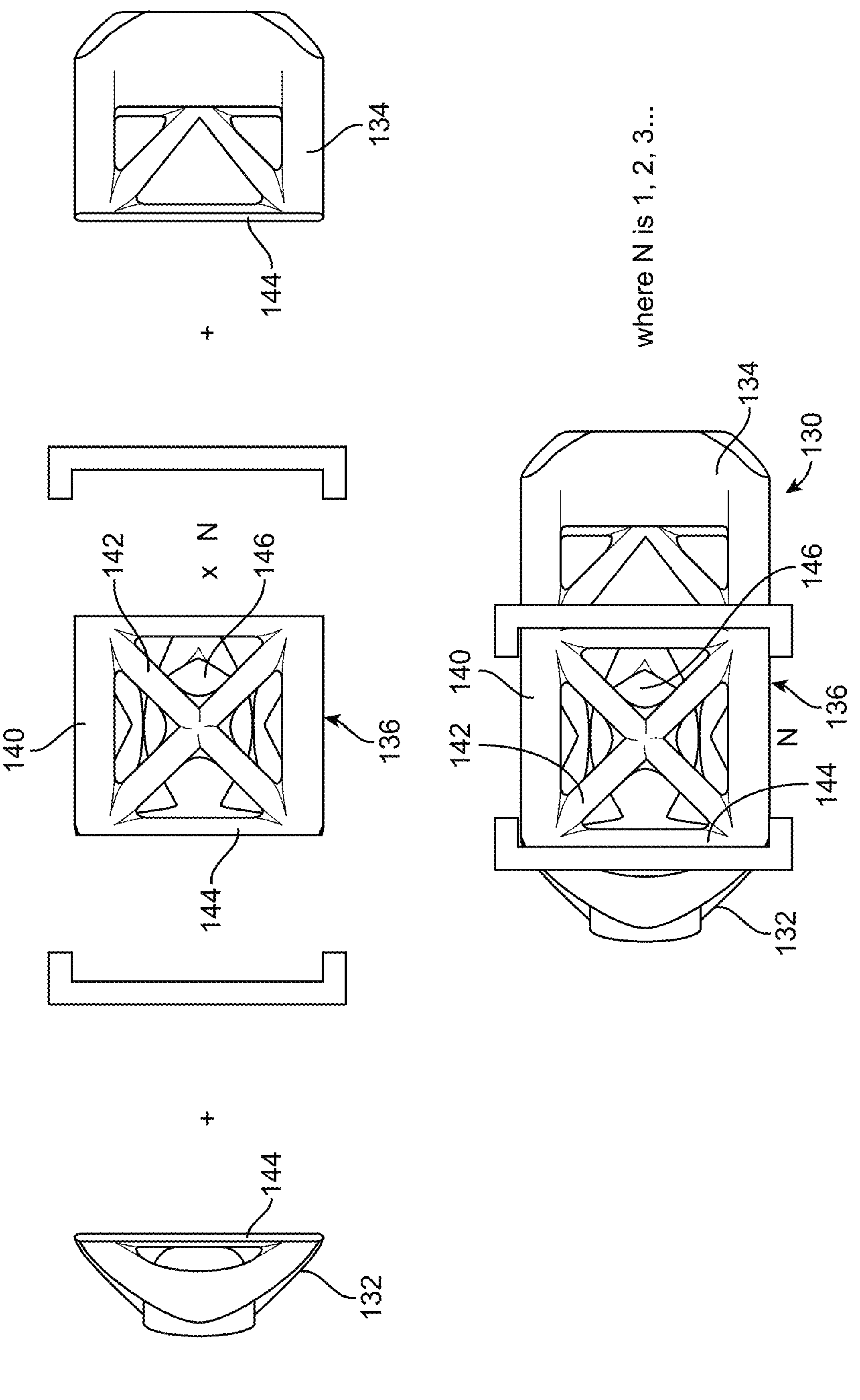
FIG. 13 illustrates an embodiment of a modular matrix implant.

The length of the implant can vary between about 25 to 95 mm. The matrix structure can be modular, as shown in FIG. 13, which allows the length of the implant to be varied by the addition of additional repeating subunits during the design and/or fabrication of the implant. For example, the modular matrix implant 130 can have a distal end portion 132, a proximal end portion 134, and one or more repeating internal portions 136. The distal end portion 132 can have a distal guide pin receptacle 138, and the proximal end portion 134 can have a proximal guide pin receptacle 136, much like the embodiments discussed above. The repeating internal portion 136 can have apex struts 140 and support struts 142, as described above. For example, as shown, the support struts 142 can have an “X” configuration and can be located between two transverse support struts 144. The two transverse support struts 144 can be half the normal transverse support struts such that when two repeating internal portions 136 are joined together, the two half support struts merge to form a whole transverse support strut. The proximal and distal end portions 132, 134 can also have a coupling portion that is formed from half transverse support struts 144 that can be merged with the half transverse support struts 144 of the repeating internal portion 136. In some embodiments, the repeating internal portion 136 can also have an internal guide pin receptacle 146

In some embodiments, the length of the repeating internal portion 136 can be about 10 mm. In other embodiments, the length can be between about 5 and 25 mm. In some embodiments, the repeating internal portion 136 can have support struts that form half an "X", such that the repeating internal portions are arranged in an alternating pattern to form "X" shaped support struts. In some embodiments, the support struts are simply diagonal struts that extend across the length of the repeating internal portion.

Methods of Implantation

The methods of implantation of the various implants described herein are described in U.S. Patent Publication No. 2011/0087294, U.S. Pat. Nos. 8,425,570, 8,444,693, 8,414,648, and 8,470,004, and U.S. Provisional Application No. 61/891,326, each of which is herein incorporated by reference in its entirety for all purposes. These methods are particularly suited for use with straight implants.

The curved implant illustrated in FIG. 12 may require modifications to the method of insertion protocols. Because the implant is curved, it may not be possible or desirable to attempt to hammer or tap the implant into the bone along a straight path using a straight guide pin, a straight drill, a straight broach and the like. Instead, it may be desirable to create and form a curved insertion path that matches the curvature of the implant.

For example, the tooling used to create the curved insertion path can have a radius of curvature that matches the radius of curvature of the implant. For example, some or all of the tooling and the implant can have a matching radius of curvature. The tooling, which can include a guide pin, a tool guide, a drill bit, a broach, and impact hammer and the like can be rotatably secured by an arm with a length equal to the radius of curvature, with one end of the arm attached to a pivot and the other end used to secure the tools and/or implant.

The rotating arm can be used to drive a curved guide pin into the bone to create a curved path through the bone, such as the ilium and the sacrum. A relatively short drill bit with a lumen for receiving the guide pin can be disposed over the curved guide pin to drill out a curved pilot bore. In some embodiments, the drill bit can be secured by the pivoting arm at the end of a curved guide and can be used to drill the curved pilot bore without the insertion of the curved guide pin.

For a curved implant with a circular cross section, the curved implant can then be advanced over the curved guide pin and into the curved insertion path that is formed by the curved pilot bore. In some embodiments, the curved implant can be held by the pivoting arm and inserted into the curved insertion path without the aid of a guide pin by rotating the curved arm.

For a rectilinear implant or more broadly a noncircular implant, the curved pilot bore can be shaped using an appropriately shaped broach that matches the overall cross-sectional shape of the implant. A curved broach, or a short broach, can be advanced over the curved guide pin if present, otherwise the curved broach or short broach can be held in the pivoting arm and advanced through the pilot bore by rotation of the pivoting arm. As the broach is advanced, it shapes the pilot bore into a shape that matches the shape of the implant.

The curved implant can then be advanced over the curved guide pin and into the curved insertion path that is formed by the curved pilot bore. In some embodiments, the curved implant can be held by the pivoting arm and inserted into the curved insertion path without the aid of a guide pin by rotating the curved arm.

More generally, the implants described herein can be used to fuse any two bone segments, such as two bones that form a joint or two bones resulting from a fracture.

The terms "about" and "approximately" and the like can mean within 5, 10, 15, 20, 25, or 30 percent.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. An implant for the fixation or fusion of a sacroiliac joint, the implant comprising:

an elongate body having a proximal end, a distal end, a longitudinal axis and a rectilinear outer profile in a cross-section transverse to the longitudinal axis, the elongate body further comprising:

a plurality of apex struts disposed between the proximal end and the distal end of the elongate body and along the longitudinal axis of the elongate body, wherein each apex strut of the plurality of apex struts is part of a first pair of apex struts with a first circumferentially adjacent apex strut, and is part of a second pair of apex struts with a second circumferentially adjacent apex strut, and a plurality of faces, wherein every pair of circumferentially adjacent apex struts has one of the plurality of faces therebetween, and wherein each of the plurality of faces includes a plurality of fenestrations, wherein each of the plurality of fenestrations in each of the plurality of faces has a fixed-size and a fixed-shape.

2. The implant of claim 1, wherein each of the plurality of faces comprises a matrix structure.

3. The implant of claim 1, wherein each of the plurality of faces comprises a matrix structure including a plurality of support struts extending between the respective pair of adjacent linear apex struts.

4. The implant of claim 3, wherein the plurality of support struts comprises a plurality of transverse support struts.

5. The implant of claim 3, wherein the plurality of support struts comprises a plurality of oblique support struts.

6. The implant of claim 3, wherein the plurality of support struts are preferentially porous with radially outer portions of the plurality of support struts being porous and radially inner portions of the plurality of support struts not porous.

7. The implant of claim 1, wherein each face includes a first set of fenestrations and a second set of fenestrations.

8. The implant of claim 7, wherein the fenestrations in the first set of fenestrations are triangular.

9. An implant for the fixation or fusion of a sacroiliac joint, the implant comprising:

an elongate body having a proximal end, a distal end, a longitudinal axis and a rectilinear outer profile in a cross-section transverse to the longitudinal axis, the elongate body further comprising:

a plurality of apex struts parallel with the longitudinal axis and disposed between the proximal end and the distal end of the elongate body, wherein each apex strut of the plurality of apex struts is part of a first pair of apex struts with a first circumferentially adjacent apex strut, and is part of a second pair of apex struts with a second circumferentially adjacent apex strut; and a plurality of faces, wherein every pair of circumferentially adjacent apex struts has one of the plurality of faces therebetween, and wherein each of the plurality of faces includes a plurality of support struts defining a plurality of fixed-size and fixed-shape fenestrations.

10. The implant of claim 9, wherein the plurality of support struts in each of the plurality of faces includes at least one of a plurality of transverse support struts or a plurality of oblique support struts.

11. The implant of claim 10, wherein the plurality of support struts in each of the plurality of faces consists of a plurality of transverse support struts and a plurality of oblique support struts.

12. The implant of claim 9, wherein each face of the plurality of faces includes a first set of fenestrations and a second set of fenestrations.

13. The implant of claim 12, wherein the fenestrations in the first set of fenestrations are triangular.

14. An implant for the fixation or fusion of a sacroiliac joint, the implant comprising:

an elongate body having a proximal end, a distal end, a longitudinal axis and a triangular outer profile in a cross-section transverse to the longitudinal axis, the elongate body further comprising:

a plurality of apex struts disposed between the proximal end and the distal end of the elongate body and along the longitudinal axis of the elongate body, wherein each apex strut of the plurality of apex struts is part of a first pair of apex struts with a first circumferentially adjacent apex strut, and is part of a second pair of apex struts with a second circumferentially adjacent apex strut; and a plurality of faces, wherein every pair of circumferentially adjacent apex struts has one of the plurality of faces therebetween, and wherein each of the plurality of faces includes a plurality of support struts forming a plurality of fixed-size and fixed-shape fenestrations in the corresponding face, wherein the plurality of apex struts are preferentially porous with radially outer portions of the plurality of apex struts being porous and radially inner portions of the plurality of apex struts are not porous, and wherein the plurality of support struts in each of the plurality of faces are preferentially porous with radially outer portions of the plurality of support struts being porous and radially inner portions of the plurality of support struts not porous.

15. The implant of claim 14, wherein the plurality of support struts in each of the plurality of faces includes at least one of a plurality of transverse support struts or a plurality of oblique support struts.

16. The implant of claim 15, wherein the plurality of support struts in each of the plurality of faces consists of a plurality of transverse support struts and a plurality of oblique support struts.

17. The implant of claim 14, wherein each face of the plurality of faces includes a first set of fenestrations and a second set of fenestrations.

18. The implant of claim 17, wherein the fenestrations in the first set of fenestrations are triangular.

* * * * *